(12) United States Patent
Amrein et al.

(10) Patent No.: US 7,528,158 B2
(45) Date of Patent: May 5, 2009

(54) INDAZOLONE DERIVATIVES USEFUL AS 11B-HSD1 INHIBITORS

(75) Inventors: Kurt Amrein, Itingen (CH); Jianping Cai, West Caldwell, NJ (US); Robert Alan Goodnow, Jr., Gillette, NJ (US); Daniel Hunziker, Moehlin (CH); Bernd Kuhn, Liestal (CH); Alexander Mayweg, Loerrach (DE); Werner Neidhart, Hagenthal le Bas (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 492 days.

(21) Appl. No.: 11/235,375

(22) Filed: Sep. 26, 2005

(65) Prior Publication Data

US 2006/0069269 A1    Mar. 30, 2006

(30) Foreign Application Priority Data

Sep. 29, 2004   (EP) .................................. 04104753

(51) Int. Cl.
*A61K 31/44* (2006.01)
*C07D 231/56* (2006.01)

(52) U.S. Cl. .................................... 514/338; 548/361.5

(58) Field of Classification Search .................. None
See application file for complete search history.

(56) References Cited

U.S. PATENT DOCUMENTS

| 5,173,496 | A | 12/1992 | Breneau et al. | |
|---|---|---|---|---|
| 6,858,638 | B2 * | 2/2005 | Damour et al. | 514/405 |
| 2003/0166689 | A1 | 9/2003 | Kurz et al. | |

FOREIGN PATENT DOCUMENTS

| WO | WO 99/47508 | 9/1999 |
|---|---|---|
| WO | WO 03/099773 | 12/2003 |
| WO | WO 2005/060963 A1 | 7/2005 |

OTHER PUBLICATIONS

Masuzaki H. et al., Science. Dec. 7, 2001; 294(5549):2166-70.
Walker et al. 1995; J. Clin. Endocrinol. Metab. 80, 31155-3159.
P.M. Stewart and Z.S. Krozowski, Vitam. Horm. 57 (1999), pp. 249-324.
Kotelevtsev Y. et al., Proc Natl Acad Sci U S A. Dec. 23, 1997;94(26):14924-9.
Masuzaki H. et al., J Clin Invest. Jul. 2003;112(1):83-90.
Rauz S. et al., QJM. Jul. 2003;96(7):481-90.
Sandeep TC. et al., Proc Natl Acad Sci U S A. Apr. 27, 2004;101(17):6734-9.

* cited by examiner

*Primary Examiner*—Kamal A Saeed
(74) *Attorney, Agent, or Firm*—George W. Johnston; Dennis P. Tramaloni; Samuel H. Megerditchian

(57) ABSTRACT

Compounds of formula (I)

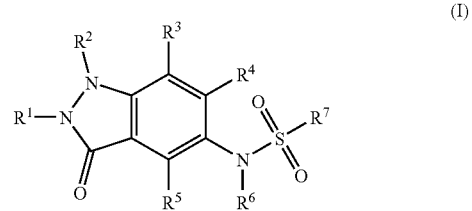

as well as pharmaceutically acceptable salts and esters thereof, wherein $R^1$ to $R^7$ have the significances given in the description and claims can be used in the form of pharmaceutical compositions.

28 Claims, No Drawings

INDAZOLONE DERIVATIVES USEFUL AS 11B-HSD1 INHIBITORS

FIELD OF THE INVENTION

The present invention is directed to novel indazolone derivatives which are useful as 11b-HSD1 inhibitors.

In particular, the invention is concerned particularly with compounds of formula (I)

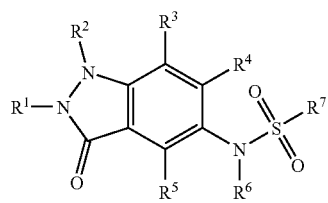

and pharmaceutically acceptable salts thereof.

All documents cited or relied upon below are expressly incorporated herein by reference.

BACKGROUND OF THE INVENTION

Glucocorticoids (cortisol in humans, corticosterone in mice and rats) are an important class of adrenocorticosteroids that regulate many metabolic and homeostatic processes and form a key component of the response to stress. Glucocorticoids act via intracellular glucocorticoid receptors and, in some tissues, mineralocorticoid receptors; both being nuclear transcription factors. Glucocorticoid action on target tissues depends not only on circulating steroid concentrations and the cellular expression of receptors, but also on intracellular enzymes that critically determine to which extent glucocorticoids gain access to receptors in an active form. 11beta-hydroxysteroid dehydrogenases (11beta-HSD's) catalyze the interconversion of the principal active 11-hydroxy-glucocorticoid (Cortisol in men) and their inactive 11-keto metabolites (cortisone in men).

The enzyme 11beta-hydroxysteroid dehydrogenase type 1 (11beta-HSD1) inter-converts inactive into active glucocorticoids, thereby playing a major role in local modulation of cellular agonist concentration and thus activation of corticosteroid receptors in target tissues. In a recent study made by F. Hoffmann-La Roche differences in gene expression in lean and obese men were analyzed using gene array technology in order to identify specific changes in gene expression that might be associated with insulin resistance or altered metabolism. This study revealed that the mRNA for 11beta-HSD1 is approximately two-fold up regulated in adipose tissue in obese individuals. Moreover, overexpressing 11beta-HSD1 in adipocytes of mice led to visceral obesity and to a syndrome-X like phenotype (Masuzaki H. et al., Science. 2001 Dec. 7; 294(5549):2166-70.). Taken together, these data very strongly support an important role of 11beta-HSD1 in the induction of obesity and the impairment of glucose homeostasis and lipid parameters. Thus, selective inhibition of this enzyme could lower blood glucose levels in Type 2 diabetic patients, normalize elevated lipid parameters and/or reduce weight in obese subjects.

The first pharmacological indication that 11beta-HSD1 inhibition in men might have beneficial effects were obtained by using carbenoxolone, an anti-ulcer drug which inhibits both 11beta-HSD1 and the related enzyme 11beta-HSD2. Treatment with carbenoxolone led to an increase in insulin sensitivity indicating that that inhibition of 11beta-HSD1 may reduce cellular cortisol levels and therefore minimizing some of its deleterious effects. (Walker et al. 1995; J. Clin. Endocrinol. Metab. 80, 31155-3159).

11beta-HSD1 is expressed in many tissues including liver, adipose tissue, vascular smooth muscles, pancreas and brain. Its activity is dependent on NADP(H) and it has a relatively low affinity for its substrate (compared to 11beta-HSD2). 11 beta-HSD1 in tissue homogenates and when purified is bidirectional, exhibiting both 11beta-dehydrogenase and 11beta-reductase reactions, with greater stability of the dehydrogenase activity (P. M. Stewart and Z. S. Krozowski, Vitam. Horm. 57 (1999), pp. 249-324). However, when the enzyme activity is tested in intact cells, the 11beta-reductase activity predominates, which regenerates active glucocorticoids from inert 11-keto forms. Such glucocorticoid regeneration will increase effective intracellular glucocorticoid levels and thereby amplifying glucocorticoid activity. It is this elevated cellular cortisol concentration that might lead to increased hepatic glucose production, adipocyte differentiation and insulin resistance.

Inhibition of 11beta-HSD1 should not only reduce the typical Syndrome-X/Diabetes associated symptoms, but it should also be save and without major side effect. Studies with the unspecific inhibitor carbenoxolone highlight the importance of developing specific 11beta-HSD1 inhibitors. The inhibition of the 11beta-HSD2 enzyme is badly tolerated and results in increased blood pressure. In contrast inhibition of 11beta-HSD1 should be well tolerated since 11beta-HSD1 knockout mice were found be healthy and to resist hyperglycemia provoked by obesity or stress (Kotelevtsev Y. et al., Proc Natl Acad Sci USA. 1997 Dec. 23; 94(26):14924-9). Similar upon starvation these mice had attenuated activation of key hepatic enzymes that are involved in gluconeogenesis. In addition, these mice had improved lipid and lipoprotein profiles suggesting that inhibition of HSD1 might be highly efficacious and safe. Recent reports indicate that 11beta-HSD1 inhibitors might also be beneficial to reduce high blood pressure (Masuzaki H. et al., J Clin Invest. 2003 July; 112(1): 83-90; Rauz S. et al., QJM. 2003 July; 96(7):481-90) to improve cognition (Sandeep T C. et al., Proc Natl Acad Sci U S A. 2004 Apr. 27; 101(17):6734-9) or to improve Alzheimer associated deficits. Taken together 11beta-HSD1 inhibition might be a save and efficacious approach to treat symptoms of diabetes, obesity and other diseases.

SUMMARY OF THE INVENTION

In one embodiment of the present invention, provided is a compound of the formula (I):

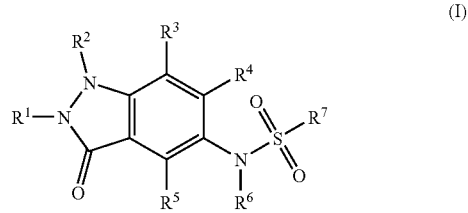

wherein:

R¹ is hydrogen, lower-alkyl, aryl, or aryl-lower-alkyl;

R² is aryl, aryl-lower-alkyl, heteroaryl, heteroaryl-lower-alkyl, cycloalkyl, cycloalkyl-lower-alkyl, fluoro-loweralkyl, or lower-alkyl, which lower-alkyl is optionally substituted with 1 to 3 substituents selected from the group consisting of OH, CN, halogen, lower-alkoxy and C(O) NR$^8$R$^9$;

R$^3$ is hydrogen, halogen, lower-alkyl, fluoro-lower-alkyl, lower-alkoxy, or fluoro-lower-alkoxy;

R$^4$ is hydrogen, halogen, lower-alkyl, fluoro-lower-alkyl, lower-alkoxy, or fluoro-lower-alkoxy;

R$^5$ is hydrogen, halogen, lower-alkyl, fluoro-lower-alkyl, lower-alkoxy, or fluoro-lower-alkoxy, R$^6$ is hydrogen or lower-alkyl;

R$^7$ is aryl, heteroaryl, fluoro-lower-alkyl, or lower-alkyl, which lower-alkyl is optionally substituted with 1 to 3 substituents selected from the group consisting of OH, CN, halogen, lower-alkoxy and cycloalkyl; and R$^8$ and R$^9$, independently from each other, are selected from the group consisting of hydrogen and lower-alkyl;

and pharmaceutically acceptable salts thereof.

In another embodiment of the present invention, provided is a process for the preparation of compounds according to claim 1, comprising the reaction of a compound of formula (II)

with a compound of formula (III)

wherein R$^1$ to R$^7$ are as defined above.

In a further embodiment of the present invention, provided is a pharmaceutical composition, comprising a therapeutically effective amount of a compound according to formula (I) and a pharmaceutically acceptable carrier and/or adjuvant.

In a yet another embodiment of the present invention, a method for the treatment and/or prophylaxis of diseases which are caused by disorders associated with the enzyme 11beta-hydroxysteroid dehydrogenase 1, particularly for the treatment and/or prophylaxis of metabolic disorders, obesity, dyslipidemiae, hypertension and/or diabetes, particularly diabetes type II, which method comprises administering an effective amount of a compound according to formula (I).

DETAILED DESCRIPTION

The compounds of formula I and their pharmaceutically acceptable salts and esters are novel and have valuable pharmacological properties. In particular they are 11b-HSD1 inhibitors and they display selectivity against the related 11beta-HSD2 enzyme. Therefore the compounds which are specific 11beta-HSD1 inhibitors represent an approach to e.g. lower blood glucose levels and normalize lipid parameters in Type 2 diabetic patients by modulating the local concentration of the active glucocorticoid cortisol in target tissue (liver, adipose tissue).

The compounds of the present invention can be used in the prophylaxis and/or treatment of metabolic disorders, obesity, dyslipidemiae, hypertension and/or diabetes, particularly diabetes Type II. The compounds of this invention can further be used in the prophylaxis and/or treatment of high ocular eye pressure, cognition, Alzheimer and/or neurodegeneration.

The compounds of the present invention can further be combined with PPAR (alpha, gamma, delta) agonists, DHEA (dehydroepiandrosterone), DPPIV inhibitors, insulin and/or lipase inhibitors, particularly orlistat.

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. Lower-alkyl groups can optionally be substituted, e.g. by OH, CN, halogen, lower-alkoxy, or aminocarbonyl. Unsubstituted lower-alkyl groups are preferred.

The term "fluoro-lower-alkyl" refers to lower-alkyl groups which are mono- or multiply substituted with fluorine. Examples of fluoro-lower-alkyl groups are e.g. CFH$_2$, CF$_2$H, CF$_3$, CF$_3$CH$_2$, CF$_3$(CH$_2$)$_2$, (CF$_3$)$_2$CH and CF$_2$H—CF$_2$.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl.

Examples of fluoro-lower-alkoxy groups are e.g. CFH$_2$—O, CF$_2$H—O, CF$_3$—O, CF$_3$CH$_2$—O, CF$_3$(CH$_2$)$_2$—O, (CF$_3$)$_2$CH—O, and CF$_2$H—CF$_2$—O.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —NH$_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups. The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "aryl", alone or in combination, relates to the phenyl or naphthyl group, preferably the phenyl group, which can optionally be substituted by 1 to 5, preferably 1 to 3, substituents independently selected from the group consisting of lower-alkyl, lower-alkoxy, halogen, hydroxy, CN, $CF_3$, amino, aminocarbonyl, carboxy, $NO_2$, dioxo-lower-alkylene (forming e.g. a benzodioxyl group), lower-alkylsufonyl, aminosulfonyl, lower-alkylcarbonyl, lower-alkylcarbonyloxy, lower-alkylcarbonyl-NH, lower-alkoxycarbonyl, fluoro-lower-alkyl, fluoro-lower-alkoxy, cycloalkyl, phenyloxy and methyl-oxadiazolyl. Preferred substituents are halogen, lower-alkyl, fluoro-lower-alkyl and CN.

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furyl, pyridinyl, pyridazinyl, oxo-pyridazinyl, pyrimidinyl, 2-oxo-pyridinyl, 2-oxo-pyrimidinyl pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl. A preferred heteroaryl group is pyridinyl. A heteroaryl group may have a substitution pattern as described earlier in connection with the term "aryl".

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and Trimethylammoniumsalt. The term "pharmaceutically acceptable salts" also refers to such salts. Salts obtained by the addition of an acid are preferred. The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

In detail, the present invention relates to compounds of formula (I)

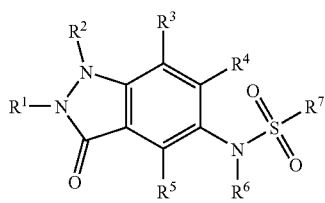

wherein
$R^1$ is hydrogen, lower-alkyl, aryl, or aryl-lower-alkyl;
$R^2$ is aryl, aryl-lower-alkyl, heteroaryl, heteroaryl-lower-alkyl, cycloalkyl, cycloalkyl-lower-alkyl, fluoro-lower-alkyl, or lower-alkyl, which lower-alkyl is optionally substituted with 1 to 3 substituents selected from the group consisting of OH, CN, halogen, lower-alkoxy and C(O)$NR^8R^9$;
$R^3$ is hydrogen, halogen, lower-alkyl, fluoro-lower-alkyl, lower-alkoxy, or fluoro-lower-alkoxy,
$R^4$ is hydrogen, halogen, lower-alkyl, fluoro-lower-alkyl, lower-alkoxy, or fluoro-lower-alkoxy;
$R^5$ is hydrogen, halogen, lower-alkyl, fluoro-lower-alkyl, lower-alkoxy, or fluoro-lower-alkoxy;
$R^6$ is hydrogen or lower-alkyl;
$R^7$ is aryl, heteroaryl, fluoro-lower-alkyl, or lower-alkyl, which lower-alkyl is optionally substituted with 1 to 3 substituents selected from the group consisting of OH, CN, halogen, lower-alkoxy and cycloalkyl;
$R^8$ and $R^9$, independently from each other, are selected from the group consisting of hydrogen and lower-alkyl;
and pharmaceutically acceptable salts thereof.

The compounds of formula I can have one or more asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates. The invention embraces all of these forms. Preferred are the compounds of formula I.

Preferred compounds of formula (I) as described above are those wherein
$R^1$ is hydrogen, lower-alkyl, aryl, or aryl-lower-alkyl;
$R^2$ is aryl, aryl-lower-alkyl, heteroaryl, heteroaryl-lower-alkyl, cycloalkyl, cycloalkyl-lower-alkyl, fluoro-lower-alkyl, or lower-alkyl, which lower-alkyl is optionally substituted with 1 to 3 substituents selected from the group consisting of OH, CN, halogen, lower-alkoxy and C(O)$NR^8R^9$;
$R^3$ is hydrogen, halogen, lower-alkyl, fluoro-lower-alkyl, lower-alkoxy, or fluoro-lower-alkoxy,
$R^4$ is hydrogen, halogen, lower-alkyl, fluoro-lower-alkyl, lower-alkoxy, or fluoro-lower-alkoxy;
$R^5$ is hydrogen, halogen, lower-alkyl, fluoro-lower-alkyl, lower-alkoxy, or fluoro-lower-alkoxy;
$R^6$ is hydrogen or lower-alkyl;
$R^7$ is aryl, heteroaryl, fluoro-lower-alkyl, or lower-alkyl, which lower-alkyl is optionally substituted with 1 to 3 substituents selected from the group consisting of OH, CN, halogen and lower-alkoxy;
$R^8$ and $R^9$, independently from each other, are selected from the group consisting of hydrogen and lower-alkyl;
and pharmaceutically acceptable salts thereof.

A preferred embodiment of the present invention relates to compounds of formula (I) as described above, wherein $R^1$ is hydrogen or lower-alkyl, preferably wherein $R^1$ is hydrogen.

Another preferred embodiment of the present invention are the compounds of formula (I), wherein $R^2$ is aryl-lower-alkyl, heteroaryl-lower-alkyl, cycloalkyl-lower-alkyl, fluoro-lower-alkyl, or lower-alkyl, which lower-alkyl is optionally substituted with 1 to 3 substituents selected from the group consisting of OH, CN, halogen, lower-alkoxy and C(O)$NR^8R^9$, wherein $R^8$ and $R^9$ are as defined above. Preferably, $R^2$ is aryl-lower-alkyl or heteroaryl-lower-alkyl, more preferably $R^2$ is benzyl or pyridinylmethyl, wherein benzyl can optionally be substituted with 1 or 2 halogen. Especially preferred are those compounds wherein $R^2$ is benzyl, 4-fluoro-benzyl, 4-chloro-benzyl, 3,4-difluoro-benzyl, or pyridin-2-ylmethyl. Other preferred compounds are those, wherein $R^2$ is aryl, particularly phenyl.

Also preferred are the compounds of formula (I), wherein $R^3$ is hydrogen. Further preferred are those compounds according to formula (I), wherein $R^4$ is hydrogen or halogen, particularly wherein $R^4$ is hydrogen, fluorine, or chlorine.

Another preferred aspect of the present invention are compounds of formula (I), wherein $R^5$ is hydrogen or halogen, particularly wherein $R^5$ is hydrogen. Other preferred compounds of formula (I) as defined above are those wherein $R^6$ is hydrogen.

In a further preferred embodiment of the present invention, $R^7$ is lower-alkyl or aryl. Particularly preferred are those compounds, wherein $R^7$ is lower-alkyl, phenyl or naphthyl, wherein phenyl can optionally be substituted with 1 to 3 substituents independently selected from the group consisting of lower-alkyl, fluoro-lower-alkyl, lower-alkoxy, fluoro-lower-alkoxy, dioxo-lower-alkylene, halogen, cyano, phenoxy and 5-methyl-[1,3,4]-oxadiazol-2-yl. More preferably, $R^7$ is phenyl substituted with 1 to 2 substituents selected from the group consisting of lower-alkyl, fluoro-lower-alkyl, halogen and cyano, particularly 3-chloro-2-methyl-phenyl, 2,3-dichloro-phenyl, 3-chloro-4-fluoro-phenyl, 3-trifluoromethyl-4-fluoro-phenyl, 3-cyano-phenyl, 2,5-difluoro-phenyl, 3-chloro-2-fluoro-phenyl, 5-chloro-2-fluoro-phenyl, or 2-chloro-phenyl. Other preferred compounds of formula (I) as described above are those, wherein $R^7$ is fluoro-lower-alkyl or lower-alkyl substituted with cyclopropyl, especially those wherein $R^7$ is cyclopropyl-methyl.

Examples of preferred compounds of formula (I) are those selected from the group consisting of:
N-(1-Benzyl-3-oxo-2,3-dihydro-1H-indazol-5-yl)-3-chloro-2-methyl-benzenesulfonamide,
N-(1-Benzyl-3-oxo-2,3-dihydro-1H-indazol-5-yl)-3-chloro-4-fluoro-benzenesulfonamide,
N-(1-Benzyl-3-oxo-2,3-dihydro-1H-indazol-5-yl)-3-trifluoromethyl-benzenesulfonamide,
N-(1-Benzyl-3-oxo-2,3-dihydro-1H-indazol-5-yl)-2,4-dichloro-benzenesulfonamide,
Naphthalene-2-sulfonic acid (1-benzyl-3-oxo-2,3-dihydro-1H-indazol-5-yl)-amide,
N-(1-Benzyl-3-oxo-2,3-dihydro-1H-indazol-5-yl)-3-chloro-4-methyl-benzenesulfonamide,
N-(1-Benzyl-3-oxo-2,3-dihydro-1H-indazol-5-yl)-4-methoxy-benzenesulfonamide,
N-(1-Benzyl-3-oxo-2,3-dihydro-1H-indazol-5-yl)-2,4-dichloro-6-methyl-benzenesulfonamide,
N-(1-Benzyl-3-oxo-2,3-dihydro-1H-indazol-5-yl)-2-trifluoromethyl-benzenesulfonamide,
N-(1-Benzyl-3-oxo-2,3-dihydro-1H-indazol-5-yl)-2,4-difluoro-benzenesulfonamide,
N-(1-Benzyl-3-oxo-2,3-dihydro-1H-indazol-5-yl)-4-propyl-benzenesulfonamide,
2,3-Dihydro-benzo[1,4]dioxine-6-sulfonic acid (1-benzyl-3-oxo-2,3-dihydro-1H-indazol-5-yl)-amide,
N-(1-Benzyl-3-oxo-2,3-dihydro-1H-indazol-5-yl)-4-chloro-2,5-dimethyl-benzenesulfonamide,
N-(1-Benzyl-3-oxo-2,3-dihydro-1H-indazol-5-yl)-4-chloro-3-trifluoromethyl-benzenesulfonamide,
N-(1-Benzyl-3-oxo-2,3-dihydro-1H-indazol-5-yl)-4-fluoro-3-trifluoromethyl-benzenesulfonamide,
N-(1-Benzyl-3-oxo-2,3-dihydro-1H-indazol-5-yl)-2-chloro-5-trifluoromethyl-benzenesulfonamide,
N-(1-Benzyl-3-oxo-2,3-dihydro-1H-indazol-5-yl)-3-phenoxy-benzenesulfonamide,
N-(1-Benzyl-3-oxo-2,3-dihydro-1H-indazol-5-yl)-3-(5-methyl-[1,3,4]oxadiazol-2-yl)-benzenesulfonamide,
N-(1-Benzyl-3-oxo-2,3-dihydro-1H-indazol-5-yl)-3-chloro-benzenesulfonamide,
N-(1-Benzyl-3-oxo-2,3-dihydro-1H-indazol-5-yl)-3-methoxy-benzenesulfonamide,
N-(1-Benzyl-3-oxo-2,3-dihydro-1H-indazol-5-yl)-3-difluoromethoxy-benzenesulfonamide,
N-(1-Benzyl-3-oxo-2,3-dihydro-1H-indazol-5-yl)-3,5-bis-trifluoromethyl-benzenesulfonamide,
Propane-2-sulfonic acid (1-benzyl-3-oxo-2,3-dihydro-1H-indazol-5-yl)-amide,
N-(1-Benzyl-3-oxo-2,3-dihydro-1H-indazol-5-yl)-3-chloro-2-N-dimethyl-benzenesulfonamide,
N-(3-Oxo-1-propyl-2,3-dihydro-1H-indazol-5-yl)-3-trifluoromethyl-benzenesulfonamide,
2,3-Dichloro-N-(3-oxo-1-propyl-2,3-dihydro-1H-indazol-5-yl)-benzenesulfonamide,
3-Chloro-4-fluoro-N-(3-oxo-1-propyl-2,3-dihydro-1H-indazol-5-yl)-benzenesulfonamide,
3-Chloro-2-methyl-N-(3-oxo-1-phenethyl-2,3-dihydro-1H-indazol-5-yl)-benzenesulfonamide,
3-Chloro-4-methyl-N-(3-oxo-1-phenethyl-2,3-dihydro-1H-indazol-5-yl)-benzenesulfonamide,
4-Chloro-2,5-dimethyl-N-(3-oxo-1-phenethyl-2,3-dihydro-1H-indazol-5-yl)-benzenesulfonamide,
N-(3-Oxo-1-phenethyl-2,3-dihydro-1H-indazol-5-yl)-3-trifluoromethyl-benzenesulfonamide,
N-(1-Isobutyl-3-oxo-2,3-dihydro-1H-indazol-5-yl)-3-trifluoromethyl-benzenesulfonamide,
3-Chloro-N-(1-isobutyl-3-oxo-2,3-dihydro-1H-indazol-5-yl)-4-methyl-benzenesulfonamide,
3-Chloro-N-(1-isobutyl-3-oxo-2,3-dihydro-1H-indazol-5-yl)-2-methyl-benzenesulfonamide,
3-Cyano-(1-isobutyl-3-oxo-2,3-dihydro-indazol-5-yl)-benzenesulfonamide,
3-Difluoromethoxy-(1-isobutyl-3-oxo-2,3-dihydro-indazol-5-yl)-benzenesulfonamide,
4-Cyano-(1-isobutyl-3-oxo-2,3-dihydro-indazol-5-yl)-benzenesulfonamide,
4-Fluoro-N-(1-isobutyl-3-oxo-2,3-dihydro-1H-indazol-5-yl)-3-trifluoromethyl-benzenesulfonamide,
3-Chloro-4-fluoro-N-(1-isobutyl-3-oxo-2,3-dihydro-1H-indazol-5-yl)-benzenesulfonamide,
2,4-Dichloro-(1-isobutyl-3-oxo-2,3-dihydro-indazol-5-yl)-5-methyl-benzenesulfonamide,
3-Chloro-N-(1-ethyl-3-oxo-2,3-dihydro-1H-indazol-5-yl)-2-methyl-benzenesulfonamide,
3-Chloro-(1-cyclopropylmethyl-3-oxo-2,3-dihydro-indazol-5-yl)-2-methyl-benzenesulfonamide,
3-Chloro-(1-cyclopropylmethyl-3-oxo-2,3-dihydro-indazol-5-yl)-4-fluoro-benzenesulfonamide,
(1-Cyclopropylmethyl-3-oxo-2,3-dihydro-indazol-5-yl)-4-fluoro-3-trifluoromethyl-benzenesulfonamide,
3-Chloro-(1-cyclopropylmethyl-3-oxo-2,3-dihydro-indazol-5-yl)-benzenesulfonamide,
2,4-Dichloro-(1-cyclopropylmethyl-3-oxo-2,3-dihydro-indazol-5-yl)-5-methyl-benzenesulfonamide,
3-Chloro-[1-(2-methoxy-ethyl)-3-oxo-2,3-dihydro-indazol-5-yl]-2-methyl-benzenesulfonamide,
4-Fluoro-[1-(2-methoxy-ethyl)-3-oxo-2,3-dihydro-indazol-5-yl]-3-trifluoromethyl-benzenesulfonamide,
3-Chloro-4-fluoro-[1-(2-methoxy-ethyl)-3-oxo-2,3-dihydro-indazol-5-yl]-benzenesulfonamide,
2,4-Dichloro-[1-(2-methoxy-ethyl)-3-oxo-2,3-dihydro-indazol-5-yl]-6-methyl-benzenesulfonamide,
3-Chloro-2-methyl-N-[3-oxo-1-(2,2,2-trifluoro-ethyl)-2,3-dihydro-1H-indazol-5-yl]-benzenesulfonamide,
4-Fluoro-[3-oxo-1-(2,2,2-trifluoro-ethyl)-2,3-dihydro-indazol-5-yl]-3-trifluoromethyl-benzenesulfonamide,
4-Fluoro-N-(3-oxo-1-pyridin-2-ylmethyl-2,3-dihydro-1H-indazol-5-yl)-3-trifluoromethyl-benzenesulfonamide, 2,4-Dichloro-6-methyl-N-(3-oxo-1-pyridin-2-ylmethyl-2,3-dihydro-1H-indazol-5-yl)-benzenesulfonamide,
3-Chloro-2-methyl-N-(3-oxo-1-pyridin-2-ylmethyl-2,3-dihydro-1H-indazol-5-yl)-benzenesulfonamide,
4-Fluoro-N-[1-(2-hydroxy-2-methyl-propyl)-3-oxo-2,3-dihydro-1H-indazol-5-yl]-3-trifluoromethyl-benzenesulfonamide,
N-(1-Benzyl-6-chloro-3-oxo-2,3-dihydro-1H-indazol-5-yl)-3-chloro-4-fluoro-benzenesulfonamide,
N-(1-Benzyl-6-chloro-3-oxo-2,3-dihydro-1H-indazol-5-yl)-4-fluoro-3-trifluoromethyl-benzenesulfonamide,
N-(1-Benzyl-6-chloro-3-oxo-2,3-dihydro-1H-indazol-5-yl)-3-chloro-2-methyl-benzenesulfonamide,
N-(1-Benzyl-6-chloro-3-oxo-2,3-dihydro-1H-indazol-5-yl)-2,3-dichloro-benzenesulfonamide,
N-(1-Benzyl-6-chloro-3-oxo-2,3-dihydro-1H-indazol-5-yl)-3-cyano-benzenesulfonamide,
N-(1-Benzyl-6-chloro-3-oxo-2,3-dihydro-1H-indazol-5-yl)-3-chloro-benzenesulfonamide,
N-(1-Benzyl-6-chloro-3-oxo-2,3-dihydro-1H-indazol-5-yl)-4-chloro-3-trifluoromethyl-benzenesulfonamide,
N-(1-Benzyl-6-chloro-3-oxo-2,3-dihydro-1H-indazol-5-yl)-3-difluoromethoxy-benzenesulfonamide,
N-(1-Benzyl-6-chloro-3-oxo-2,3-dihydro-1H-indazol-5-yl)-2-trifluoromethyl-benzenesulfonamide,
N-(1-Benzyl-6-chloro-3-oxo-2,3-dihydro-1H-indazol-5-yl)-3-trifluoromethoxy-benzenesulfonamide,
N-(1-Benzyl-6-chloro-3-oxo-2,3-dihydro-1H-indazol-5-yl)-2,5-difluoro-benzenesulfonamide,
N-(1-Benzyl-6-chloro-3-oxo-2,3-dihydro-1H-indazol-5-yl)-2,4-dichloro-benzenesulfonamide,
N-(1-Benzyl-6-chloro-3-oxo-2,3-dihydro-1H-indazol-5-yl)-3-chloro-2-fluoro-benzenesulfonamide,
N-(1-Benzyl-6-chloro-3-oxo-2,3-dihydro-1H-indazol-5-yl)-3-trifluoromethyl-benzenesulfonamide,
N-(1-Benzyl-6-chloro-3-oxo-2,3-dihydro-1H-indazol-5-yl)-5-chloro-2-fluoro-benzenesulfonamide,
N-(1-Benzyl-6-chloro-3-oxo-2,3-dihydro-1H-indazol-5-yl)-2-chloro-benzenesulfonamide,
(1-Benzyl-4-chloro-3-oxo-2,3-dihydro-indazol-5-yl)-3-chloro-2-methyl-benzenesulfonamide,
N-(1-Benzyl-6-fluoro-3-oxo-2,3-dihydro-1H-indazol-5-yl)-4-fluoro-3-trifluoromethyl-benzenesulfonamide,
N-(1-Benzyl-6-fluoro-3-oxo-2,3-dihydro-1H-indazol-5-yl)-2,3-dichloro-benzenesulfonamide,
N-(1-Benzyl-6-fluoro-3-oxo-2,3-dihydro-1H-indazol-5-yl)-2,4-dichloro-benzenesulfonamide,
N-(1-Benzyl-6-fluoro-3-oxo-2,3-dihydro-1H-indazol-5-yl)-3-chloro-2-fluoro-benzenesulfonamide,
N-(1-Benzyl-6-fluoro-3-oxo-2,3-dihydro-1H-indazol-5-yl)-5-chloro-2-fluoro-benzenesulfonamide,
N-(1-Benzyl-6-fluoro-3-oxo-2,3-dihydro-1H-indazol-5-yl)-3-trifluoromethoxy-benzenesulfonamide,
3-Chloro-N-[1-(4-fluoro-benzyl)-3-oxo-2,3-dihydro-1H-indazol-5-yl]-benzenesulfonamide,
3-Difluoromethoxy-N-[1-(4-fluoro-benzyl)-3-oxo-2,3-dihydro-1H-indazol-5-yl]-benzenesulfonamide,
4-Fluoro-N-[1-(4-fluoro-benzyl)-3-oxo-2,3-dihydro-1H-indazol-5-yl]-3-trifluoromethyl-benzenesulfonamide,
2,3-Dihydro-benzo[1,4]dioxine-6-sulfonic acid [1-(4-fluoro-benzyl)-3-oxo-2,3-dihydro-1H-indazol-5-yl]-amide,
2,4-Dichloro-N-[1-(4-fluoro-benzyl)-3-oxo-2,3-dihydro-1H-indazol-5-yl]-6-methyl-benzenesulfonamide,
5-Chloro-2,4-difluoro-N-[1-(4-fluoro-benzyl)-3-oxo-2,3-dihydro-1H-indazol-5-yl]-benzenesulfonamide,
4-Chloro-2,5-difluoro-N-[1-(4-fluoro-benzyl)-3-oxo-2,3-dihydro-1H-indazol-5-yl]-benzenesulfonamide,
3-Chloro-[1-(4-fluoro-benzyl)-3-oxo-2,3-dihydro-indazol-5-yl]-2-methyl-benzenesulfonamide,
3-Cyano-[1-(4-fluoro-benzyl)-3-oxo-2,3-dihydro-indazol-5-yl]-benzenesulfonamide,
Naphthalene-1-sulfonic acid [1-(4-fluoro-benzyl)-3-oxo-2,3-dihydro-1H-indazol-5-yl]-amide,
3-Chloro-4-fluoro-N-[1-(4-fluoro-benzyl)-3-oxo-2,3-dihydro-1H-indazol-5-yl]-benzenesulfonamide,
3-Chloro-[1-(3,4-difluoro-benzyl)-3-oxo-2,3-dihydro-indazol-5-yl]-2-methyl-benzenesulfonamide,
3-Chloro-[1-(3,4-difluoro-benzyl)-3-oxo-2,3-dihydro-indazol-5-yl]-4-fluoro-benzenesulfonamide,
[1-(3,4-Difluoro-benzyl)-3-oxo-2,3-dihydro-indazol-5-yl]-4-fluoro-3-trifluoromethyl-benzenesulfonamide,
3-Chloro-[1-(3,4-difluoro-benzyl)-3-oxo-2,3-dihydro-indazol-5-yl]-benzenesulfonamide,
[1-(3,4-Difluoro-benzyl)-3-oxo-2,3-dihydro-indazol-5-yl]-3-trifluoromethoxy-benzenesulfonamide,
2,4-Dichloro-[1-(3,4-difluoro-benzyl)-3-oxo-2,3-dihydro-indazol-5-yl]-5-methyl-benzenesulfonamide,
3,4-Dichloro-[1-(3,4-difluoro-benzyl)-3-oxo-2,3-dihydro-indazol-5-yl]-benzenesulfonamide,
4,5-Dichloro-[1-(3,4-difluoro-benzyl)-3-oxo-2,3-dihydro-indazol-5-yl]-2-fluoro-benzenesulfonamide,
2,4,5-Trichloro-[1-(3,4-difluoro-benzyl)-3-oxo-2,3-dihydro-indazol-5-yl]-benzenesulfonamide,
2,3-Dichloro-[1-(3,4-difluoro-benzyl)-3-oxo-2,3-dihydro-indazol-5-yl]-benzenesulfonamide,
2,4-Dichloro-[1-(3,4-difluoro-benzyl)-3-oxo-2,3-dihydro-indazol-5-yl]-6-methyl-benzenesulfonamide,
3-Chloro-N-[1-(2,4-difluoro-benzyl)-3-oxo-2,3-dihydro-1H-indazol-5-yl]-4-fluoro-benzenesulfonamide,
N-[1-(2,4-Difluoro-benzyl)-3-oxo-2,3-dihydro-1H-indazol-5-yl]-4-fluoro-3-trifluoromethyl-benzenesulfonamide,
3-Chloro-N-[-(2,4-difluoro-benzyl)-3-oxo-2,3-dihydro-1H-indazol-5-yl]-2-methyl-benzenesulfonamide,
N-[1-(4-Chloro-benzyl)-3-oxo-2,3-dihydro-1H-indazol-5-yl]-4-fluoro-3-trifluoromethyl-benzenesulfonamide,
3-Chloro-N-[1-(4-chloro-benzyl)-3-oxo-2,3-dihydro-1H-indazol-5-yl]-2-methyl-benzenesulfonamide,
2,3-Dichloro-N-[1-(4-chloro-benzyl)-3-oxo-2,3-dihydro-1H-indazol-5-yl]-benzenesulfonamide,
Naphthalene-1-sulfonic acid [1-(4-chloro-benzyl)-3-oxo-2,3-dihydro-1H-indazol-5-yl]-amide,
3-Chloro-N-[1-(2-chloro-4-fluoro-benzyl)-3-oxo-2,3-dihydro-1H-indazol-5-yl]-2-methyl-benzenesulfonamide,
Naphthalene-1-sulfonic acid [1-(2-chloro-4-fluoro-benzyl)-3-oxo-2,3-dihydro-1H-indazol-5-yl]-amide,
2,3-Dichloro-N-[1-(2-chloro-4-fluoro-benzyl)-3-oxo-2,3-dihydro-1H-indazol-5-yl]-benzenesulfonamide,
N-[1-(2-Chloro-4-fluoro-benzyl)-3-oxo-2,3-dihydro-1H-indazol-5-yl]-4-fluoro-3-trifluoromethyl-benzenesulfonamide,
N-[1-(2-Chloro-4-fluoro-benzyl)-3-oxo-2,3-dihydro-1H-indazol-5-yl]-3-difluoromethoxy-benzenesulfonamide,
N-[1-(2-Chloro-4-fluoro-benzyl)-3-oxo-2,3-dihydro-1H-indazol-5-yl]-3-trifluoromethoxy-benzenesulfonamide,
3-Chloro-N-[1-(2-cyano-ethyl)-3-oxo-2,3-dihydro-1H-indazol-5-yl]-2-methyl-benzenesulfonamide,
N-[1-(2-Cyano-ethyl)-3-oxo-2,3-dihydro-1H-indazol-5-yl]-4-fluoro-3-trifluoromethyl-benzenesulfonamide,
2,4-Dichloro-N-[1-(2-cyano-ethyl)-3-oxo-2,3-dihydro-1H-indazol-5-yl]-6-methyl-benzenesulfonamide,
3-Chloro-N-[1-(2-cyano-ethyl)-3-oxo-2,3-dihydro-1H-indazol-5-yl]-4-fluoro-benzenesulfonamide, N-[6-Chloro-1-(2-chloro-benzyl)-3-oxo-2,3-dihydro-1H-indazol-5-yl]-4-fluoro-3-trifluoromethyl-benzenesulfonamide,
5-Chloro-N-[6-chloro-1-(2-chloro-benzyl)-3-oxo-2,3-dihydro-1H-indazol-5-yl]-2-benzenesulfonamide,
2,3-Dichloro-N-[6-chloro-1-(2-chloro-benzyl)-3-oxo-2,3-dihydro-1H-indazol-5-yl]-benzenesulfonamide,
3-Chloro-N-(6-chloro-3-oxo-1-pyridin-2-ylmethyl-2,3-dihydro-1H-indazol-5-yl)-2-methyl-benzenesulfonamide,
N-(6-Chloro-3-oxo-1-pyridin-2-ylmethyl-2,3-dihydro-1H-indazol-5-yl)-4-fluoro-3-trifluoromethyl-benzenesulfonamide,
2-[5-(3-Chloro-2-methyl-benzenesulfonylamino)-3-oxo-2,3-dihydro-indazol-1-yl]-methyl-acetamide,
2,4-Dichloro-[1-(3,4-difluoro-benzyl)-2-methyl-3-oxo-2,3-dihydro-indazol-5-yl]-6-methyl-benzenesulfonamide, and
3-Chloro-[1-(3,4-difluoro-benzyl)-2-methyl-3-oxo-2,3-dihydro-indazol-5-yl]-2-methyl-benzenesulfonamide, and pharmaceutically acceptable salts thereof.

Examples of particularly preferred compounds of formula (I) are those selected from the group consisting of:
N-(1-Benzyl-6-chloro-3-oxo-2,3-dihydro-1H-indazol-5-yl)-3-chloro-2-methyl-benzenesulfonamide,
N-(1-Benzyl-6-chloro-3-oxo-2,3-dihydro-1H-indazol-5-yl)-2,5-difluoro-benzenesulfonamide,
N-(1-Benzyl-6-chloro-3-oxo-2,3-dihydro-1H-indazol-5-yl)-3-chloro-2-fluoro-benzenesulfonamide,
N-(1-Benzyl-6-chloro-3-oxo-2,3-dihydro-1H-indazol-5-yl)-2-chloro-benzenesulfonamide,
N-(1-Benzyl-6-fluoro-3-oxo-2,3-dihydro-1H-indazol-5-yl)-3-chloro-2-fluoro-benzenesulfonamide,
N-(1-Benzyl-6-fluoro-3-oxo-2,3-dihydro-1H-indazol-5-yl)-2,3-dichloro-benzenesulfonamide,
N-(1-Benzyl-6-fluoro-3-oxo-2,3-dihydro-1H-indazol-5-yl)-5-chloro-2-fluoro-benzenesulfonamide,
N-(1-Benzyl-3-oxo-2,3-dihydro-1H-indazol-5-yl)-3-chloro-2-methyl-benzenesulfonamide,
3-Cyano-[1-(4-fluoro-benzyl)-3-oxo-2,3-dihydro-indazol-5-yl]-benzenesulfonamide,
2,3-Dichloro-N-[1-(4-chloro-benzyl)-3-oxo-2,3-dihydro-1H-indazol-5-yl]-benzenesulfonamide,
3-Chloro-N-[1-(4-chloro-benzyl)-3-oxo-2,3-dihydro-1H-indazol-5-yl]-2-methyl-benzenesulfonamide,
4-Fluoro-N-[1-(4-fluoro-benzyl)-3-oxo-2,3-dihydro-1H-indazol-5-yl]-3-trifluoromethyl-benzenesulfonamide,
3-Chloro-4-fluoro-N-[1-(4-fluoro-benzyl)-3-oxo-2,3-dihydro-1H-indazol-5-yl]-benzenesulfonamide,
3-Chloro-[1-(3,4-difluoro-benzyl)-3-oxo-2,3-dihydro-indazol-5-yl]-2-methyl-benzenesulfonamide,
N-[1-(4-Chloro-benzyl)-3-oxo-2,3-dihydro-1H-indazol-5-yl]-4-fluoro-3-trifluoromethyl-benzenesulfonamide, and
3-Chloro-2-methyl-N-(3-oxo-1-pyridin-2-ylmethyl-2,3-dihydro-1H-indazol-5-yl)-benzenesulfonamide, and pharmaceutically acceptable salts thereof.

Other examples of preferred compounds of formula (I) are those selected from the group consisting of:
2,3-Dichloro-N-(6-chloro-3-oxo-1-pyridin-2-ylmethyl-2,3-dihydro-1H-indazol-5-yl)-benzenesulfonamide,
N-(1-Benzyl-6-fluoro-3-oxo-2,3-dihydro-1H-indazol-5-yl)-2,4-difluoro-benzenesulfonamide,
2,4-Difluoro-N-(3-oxo-1-phenyl-2,3-dihydro-1H-indazol-5-yl)-benzenesulfonamide,
3-Chloro-2-fluoro-N-(3-oxo-1-phenyl-2,3-dihydro-1H-indazol-5-yl)-benzenesulfonamide,
N-(1-Benzyl-6-fluoro-3-oxo-2,3-dihydro-1H-indazol-5-yl)-3-cyano-benzenesulfonamide,
Propane-2-sulfonic acid (1-benzyl-6-fluoro-3-oxo-2,3-dihydro-1H-indazol-5-yl)-amide,
3-Cyano-N-(3-oxo-1-phenyl-2,3-dihydro-1H-indazol-5-yl)-benzenesulfonamide,
2,2,2-Trifluoro-ethanesulfonic acid (1-benzyl-6-fluoro-3-oxo-2,3-dihydro-1H-indazol-5-yl)-amide,
Propane-2-sulfonic acid (1-benzyl-6-chloro-3-oxo-2,3-dihydro-1H-indazol-5-yl)-amide,
Propane-2-sulfonic acid [6-chloro-1-(4-chloro-benzyl)-3-oxo-2,3-dihydro-1H-indazol-5-yl]-amide,
N-(1-Benzyl-6-fluoro-3-oxo-2,3-dihydro-1H-indazol-5-yl)-trifluoro-methanesulfonamide,
Propane-2-sulfonic acid (1-isobutyl-3-oxo-2,3-dihydro-1H-indazol-5-yl)-amide,
Propane-2-sulfonic acid [1-(3,4-difluoro-benzyl)-3-oxo-2,3-dihydro-1H-indazol-5-yl]-amide,
Propane-2-sulfonic acid [1-(2-methoxy-ethyl)-3-oxo-2,3-dihydro-1H-indazol-5-yl]-amide, and
N-(1-Benzyl-3-oxo-2,3-dihydro-1H-indazol-5-yl)-C-cyclopropyl-methanesulfonamide and pharmaceutically acceptable salts thereof.

Another example of a particularly preferred compound of formula (I) is:
N-(1-Benzyl-3-oxo-2,3-dihydro-1H-indazol-5-yl)-C-cyclopropyl-methanesulfonamide and pharmaceutically acceptable salts thereof.

It will be appreciated that the compounds of the present invention may be derivatized at functional groups to provide derivatives which are capable of conversion back to the parent compound in vivo. Physiologically acceptable and metabolically labile compounds, which are capable of producing the parent compounds of general formula (I) in vivo are also within the scope of the present invention.

A further aspect of the present invention is the process for the preparation of compounds as defined above comprising the reaction of a compound of formula (II)

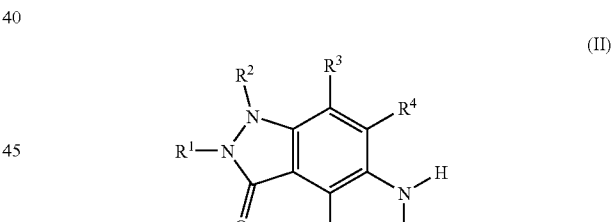

with a compound of formula (III)

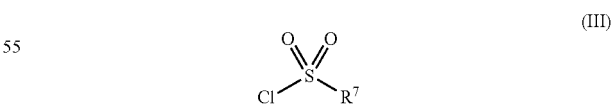

wherein $R^1$ to $R^7$ are as defined above.

Such a process can be carried out under conditions known to the person skilled in the art, e.g. in the presence of a base such as triethylamine or (4-dimethylamino)-pyridine (DMAP) in a solvent such THF, ethanol, methylene chloride DMF or DMSO, or in pyridine as a solvent, with or without the addition of a base such as triethylamine or DMAP, at room temperature or at elevated temperatures.

The invention further relates to compounds of formula (I) as described above, when prepared by a process as defined above.

The preparation of compounds of formula I of the present invention may be carried out in sequential or convergent synthetic routes. Syntheses of the invention are shown in the following schemes. The skills required for carrying out the reaction and purification of the resulting products are known to those persons skilled in the art. The substituents and indices used in the following description of the processes have the significance given above unless indicated to the contrary.

In general, compounds of type I are readily accessible by sulfonylation of appropriately substituted 5-amino-1,2-dihydro-indazol-3-one of formula IIa (R6=H) with sulfonyl chlorides, under various conditions that are known to persons skilled in the art. Examples of such conditions are—as indicated in Scheme 1 below—e.g. pyridine at elevated temperatures or THF under reflux conditions in the presence of a base such as potassium carbonate, sodium carbonate, sodium hydride, triethyl amine or the like. The sulfonyl chlorides are either commercially available or known in the literature or available in analogy to known procedures to those persons skilled in the art Scheme 1:

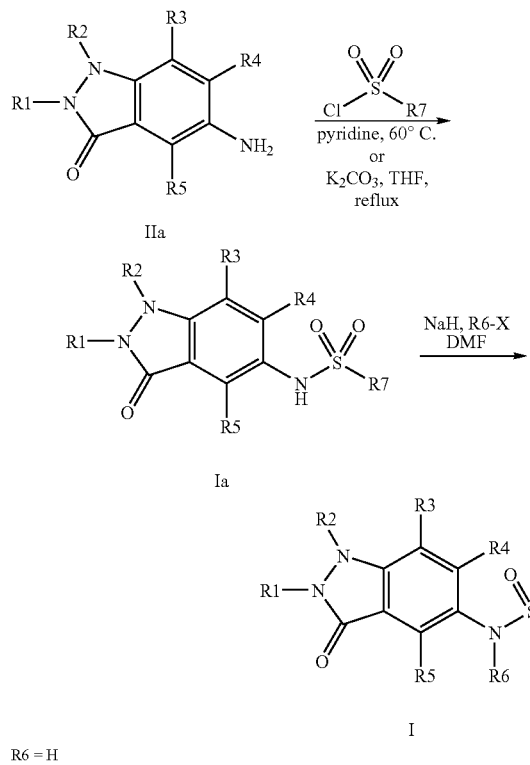

R6 = H

Optionally, compounds of formula Ia with R6=H obtained in this way can be further substituted at the sulfonamide nitrogen by treatment with a base such as sodium hydride, cesium carbonate, potassium carbonate or the like in a solvent such as DMF or THF or similar followed by alkylation of the resulting anion with an alkyl halide such as methyl iodide, ethyl bromide, benzyl bromide or the like in order to introduce the desired R6 substituent. Optionally, R6 can be introduced via alkylation of compound of formula Ia by procedures known to those persons skilled in the art.

Appropriately substituted 5-amino-1,2-dihydro-indazol-3-ones of formula IIa are either known in the literature or can be made in analogy to literature procedures from known starting materials according to scheme 2—e.g. by condensation of the appropriately functionalized 2-fluorobenzoic acid of formula III with hydrazine hydrate in ethanol and cyclization under acidic conditions, followed by alkylation with R2-X to afford compounds of formula IVa (R6=H), an optional alkylation with R1-X (under thermal or basic conditions in analogy to procedures described in *Heterocycles* 1997, 45, 129-36 or *J. Med. Chem.* 1991, 34, 1492-1503) to afford compounds of formula IV, and hydrogenation of the nitro group. (Schindler et al., *Arch. Pharm. Pharm. Med. Chem.*, 1998, 331,13-21).

Alternatively, appropriately substituted 5-amino-1,2-dihydro-indazol-3-ones of formula II are prepared according to the general Scheme 3 via a one-operation condensation of the appropriately functionalized 2-fluorobenzoic acid of formula III with an appropriately substituted hydrazine R1NHNH$_2$ of formula V in the presence of a coupling agent in DMF, followed by an optional alkylation with R1-X (under thermal or basic conditions in analogy to procedures described in *Heterocycles* 1997, 45, 129-36 or *J. Med. Chem.* 1991, 34, 1492-1503) and a reduction of the nitro group. 5-Amino-1,2-dihydro-indazol-3-ones of formula II with R2=aryl, heteroaryl can also be prepared in analogy to Menon et al., *Combin. Chem. and High-Throughput Screen.*2003, 6, 471-480. The appropriately substituted starting materials of formula III are either commercially available or are known in the literature or were prepared in analogy to literature procedures from known starting materials. The corresponding substituted hydrazines of formula V are either commercially available or are known in the literature or synthesised in analogy to literature procedures (such as *J. Org. Chem.* 1984, 49, 336-42; *J. Am. Chem. Soc.* 1986, 108, 7981-4 or *Bioorg. Med. Chem.* 2004, 12, 1357-1366).

Scheme 2:

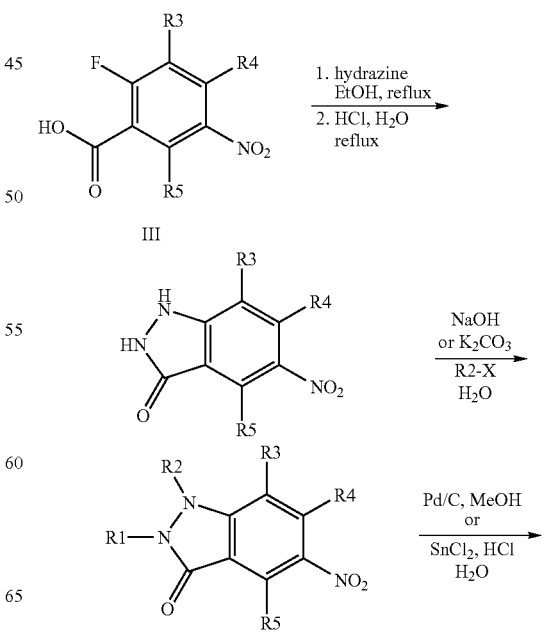

-continued

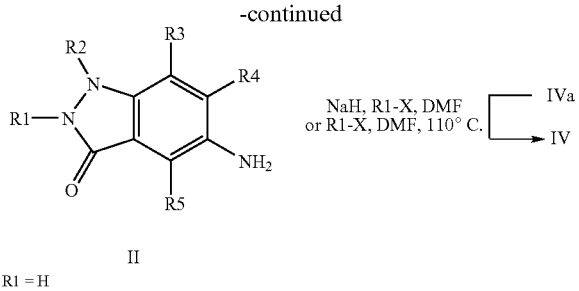

Scheme 3:

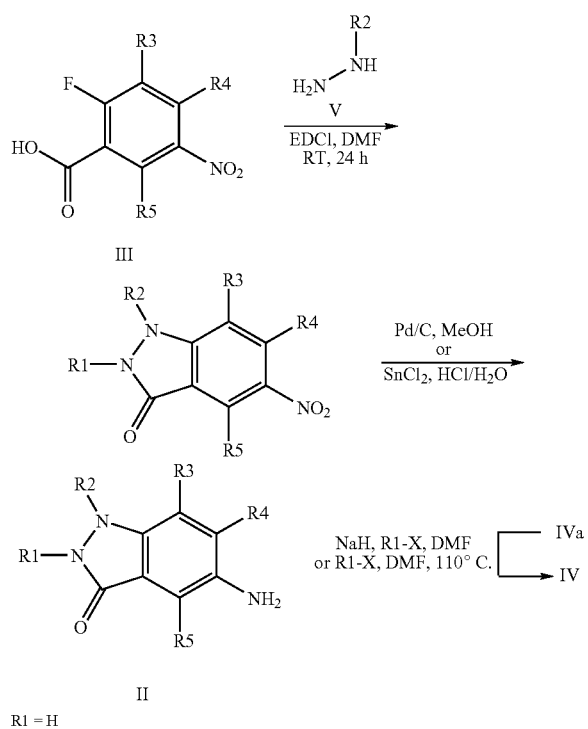

As described above, the compounds of formula (I) of the present invention can be used as medicaments for the treatment and/or prevention of diseases which are caused by disorders associated with the enzyme 11beta-hydroxysteroid dehydrogenase 1 (11bHSD1). Examples of such diseases are metabolic disorders, obesity, dyslipidemiae, hypertension and/or diabetes, particularly diabetes type II. The compounds of this invention can further be used in the prophylaxis and/or treatment of high ocular eye pressure, cognition, Alzheimer and/or neurodegeneration.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prevention of diseases which are caused by disorders associated with the enzyme 11beta-hydroxysteroid dehydrogenase 1 (11bHSD1), particularly as therapeutic active substances for the treatment and/or prevention of metabolic disorders, obesity, dyslipidemiae, hypertension and/or diabetes, particularly diabetes type II.

The invention further relates to a method for the treatment and/or prophylaxis of diseases which are caused by disorders associated with the enzyme 11beta-hydroxysteroid dehydrogenase 1, particularly for the treatment and/or prophylaxis of metabolic disorders, obesity, dyslipidemiae, hypertension and/or diabetes, particularly diabetes type II, which method comprises administering an effective amount of a compound as defined above.

In another embodiment, the present invention relates to the use of compounds as defined above for the therapeutic and/or prophylactic treatment of diseases which are caused by disorders associated with the enzyme 11beta-hydroxysteroid dehydrogenase 1, particularly for therapeutic and/or prophylactic treatment of metabolic disorders) obesity, dyslipidemiae, hypertension and/or diabetes, particularly type II diabetes.

The invention further relates to the use of compounds as defined above for the preparation of medicaments for the treatment and prophylaxis of diseases which are caused by disorders associated with the enzyme 11beta-hydroxysteroid dehydrogenase 1, particularly for the treatment and prophylaxis of metabolic disorders, obesity, dyslipidemiae, hypertension and/or diabetes, particularly type II diabetes.

Prevention and/or treatment of type II diabetes is the preferred indication.

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by examples, which have no limiting character.

EXAMPLES

Example 1

N-(1-Benzyl-3-oxo-2,3-dihydro-1H-indazol-5-yl)-3-chloro-2-methyl-benzenesulfonamide Step A] 1-Benzyl-5-nitro-1,2-dihydro-indazol-3-one To a solution of 2-fluoro-5-nitrobenzoic acid (0.5 g) in DMF (9 mL) was added TBTU (1.04 g) followed by N-ethyldiisopropylamine (2.3 mL). After 10 minutes benzylhydrazine.2HCl (0.63 g) was added. The reaction mixture was stirred at ambient temperature for 22 hours and the reaction was poured onto aqueous 1N HCl solution and extracted with EtOAc. The organic layer was washed with brine, dried over sodium sulfate, filtered and evaporated in vacuo. Purification via ISCO combiflash chromatography afforded pure desired 1-benzyl-5-nitro-1,2-dihydro-indazol-3-one (0.26 g) as a yellow solid. MS (ESI$^-$):268.3 ([M−H]$^-$).

Step B] 5-Amino-1-benzyl-1,2-dihydro-indazol-3-one

To a solution of 1-benzyl-5-nitro-1,2-dihydro-indazol-3-one (0.44 g) in MeOH (50 mL) was added Pd/C(10%) catalyst (0.1 g) and the reaction mixture was stirred for four hours at ambient temperature under a hydrogen atmosphere using a balloon. After this time the reaction mixture was filtered through Celite® which was washed with more EtOAc. The combined organic solution was evaporated in vacuo for afford the desired 5-amino-1-benzyl-1,2-dihydro-indazol-3-one (0.39 g) which was taken into the next reaction without further purification. MS (ESI$^+$): 240.1 ([M+H]$^+$).

Step C] N-(1-Benzyl-3-oxo-2,3-dihydro-1H-indazol-5-yl)-3-chloro-2-methyl-benzenesulfonamide To a solution of 5-amino-1-benzyl-1,2-dihydro-indazol-3-one (0.04 g) in pyridine (1 mL) was added 3-chloro-2-methylbenzenesulfonylchloride (0.038 g) in one go. The solution was stirred at 60° C. for 24 hours. The pyridine was then removed in vacuo and the residue was dissolved in EtOAc/water and separated. The aqueous phase was extracted a further two times with EtOAc and the combined organic phases were washed with brine and dried over sodium sulfate. The drying agent was removed by filtration and the volatiles were removed in vacuo to afford a crude residue. The crude material was purified via flash column chromatography eluting with EtOAc/nHeptane/1% AcOH) to afford the desired N-(1-benzyl-3-oxo-2,3-dihydro-1H-indazol-5-yl)-3-chloro-2-methyl-benzenesulfonamide (0.015 g) as a pale yellow powder. MS (ESI$^+$): 428.4 ([M+H]$^+$).

Example 2

N-(1-Benzyl-3-oxo-2,3-dihydro-1H-indazol-5-yl)-3-chloro-4-fluoro-benzenesulfonamide This material was obtained in analogy to example 1 using 5-amino-1-benzyl-1,2-dihydro-indazol-3-one and 3-chloro-4-fluoro-benzenesulfonyl chloride as an orange solid. MS (ESI$^-$): 430.3 ([M−H]$^-$).

Example 3

N-(1-Benzyl-3-oxo-2,3-dihydro-1H-indazol-5-yl)-3-trifluoromethyl-benzenesulfonamide This material was obtained in analogy to example 1 using 5-amino-1-benzyl-1,2-dihydro-indazol-3-one and 3-(trifluoromethyl)benzenesulfonyl chloride as a light yellow solid. MS (ESI$^+$): 448.1 ([M+H]$^+$).

Example 4

N-(1-Benzyl-3-oxo-2,3-dihydro-1H-indazol-5-yl)-2,4-dichloro-benzenesulfonamide

This material was obtained in analogy to example 1 using 5-amino-1-benzyl-1,2-dihydro-indazol-3-one and 2,4-dichlorobenzenesulfonyl chloride as a light yellow solid. MS (ESI$^-$): 446.1 ([M−H]$^-$).

Example 5

Naphthalene-2-sulfonic acid (1-benzyl-3-oxo-2,3-dihydro-1H-indazol-5-yl)-amide

This material was obtained in analogy to example 1 using 5-amino-1-benzyl-1,2-dihydro-indazol-3-one and 1-naphthalenebenzenesulfonyl chloride as a light yellow solid. MS (ESI$^-$): 428.4 ([M−H]$^-$).

Example 6

N-(1-Benzyl-3-oxo-2,3-dihydro-1H-indazol-5-yl)-3-chloro-4-methyl-benzenesulfonamide This material was obtained in analogy to example 1 using 5-amino-1-benzyl-1,2-dihydro-indazol-3-one and 3-chloro-4-methylbenzenesulfonyl chloride as a light yellow solid. MS (ESI$^+$): 428.4 ([M+H]$^+$).

Example 7

N-(1-Benzyl-3-oxo-2,3-dihydro-1H-indazol-5-yl)-4-methoxy-benzenesulfonamide

This material was obtained in analogy to example 1 using 5-amino-1-benzyl-1,2-dihydro-indazol-3-one and 4-methoxybenzenesulfonyl chloride as a light yellow solid.

Example 8

N-(1-Benzyl-3-oxo-2,3-dihydro-1H-indazol-5-yl)-2,4-dichloro-6-methyl-benzenesulfonamide This material was obtained in analogy to example 1 using 5-amino-1-benzyl-1,2-dihydro-indazol-3-one and 2,4-dichloro-6-methylbenzenesulfonyl chloride as a brown solid. MS (ESI$^-$): 460.1 ([M−H]$^-$).

Example 9

N-(1-Benzyl-3-oxo-2,3-dihydro-1H-indazol-5-yl)-2-trifluoromethyl-benzenesulfonamide This material was obtained in analogy to example 1 using 5-amino-1-benzyl-1,2-dihydro-indazol-3-one and 2-trifluoromethylbenzenesulfonyl chloride as a white solid. MS (ESI$^-$): 446.1 ([M−H]$^-$).

Example 10

N-(1-Benzyl-3-oxo-2,3-dihydro-1H-indazol-5-yl)-2,4-difluoro-benzenesulfonamide

This material was obtained in analogy to example 1 using 5-amino-1-benzyl-1,2-dihydro-indazol-3-one and 2,4-difluorobenzenesulfonyl chloride as a brown solid. MS (ESI$^-$): 414.1 ([M−H]$^-$).

Example 11

N-(1-Benzyl-3-oxo-2,3-dihydro-1H-indazol-5-yl)-4-propyl-benzenesulfonamide

This material was obtained in analogy to example 1 using 5-amino-1-benzyl-1,2-dihydro-indazol-3-one and 4-propyl-benzenesulfonyl chloride as a light yellow solid.

Example 12

2,3-Dihydro-benzo[1,4]dioxine-6-sulfonic acid (1-benzyl-3-oxo-2,3-dihydro-1H-indazol-5-yl)-amide This material was obtained in analogy to example 1 using 5-amino-1-benzyl-1,2-dihydro-indazol-3-one and 2,3-dihydro-1,4-benzodioxine-6-sulfonyl chloride as an off-white solid. MS (ESI$^+$): 438.1 ([M+H]$^+$).

Example 13

N-(1-Benzyl-3-oxo-2,3-dihydro-1H-indazol-5-yl)-4-chloro-2,5-dimethyl-benzenesulfonamide This material was obtained in analogy to example 1 using 5-amino-1-benzyl-1,2-dihydro-indazol-3-one (0.040 g) and 4-chloro-2,5-dimethylsulfonylchloride as an off-white solid. MS (ESI$^+$): 442.1 ([M+H]$^+$).

Example 14

N-(1-Benzyl-3-oxo-2,3-dihydro-H-indazol-5-yl)-4-chloro-3-trifluoromethyl-benzenesulfonamide This material was obtained in analogy to example 1 using 5-amino-1-benzyl-1,2-dihydro-indazol-3-one and 3-trifluoromethyl-4-chlorobenzenesulfonylchloride as a white solid. MS (ESI$^+$): 482.3 ([M+H]$^+$).

Example 15

N-(1-Benzyl-3-oxo-2,3-dihydro-1H-indazol-5-yl)-4-fluoro-3-trifluoromethyl-benzenesulfonamide This material was obtained in analogy to example 1 using 5-amino-1-benzyl-1,2-dihydro-indazol-3-one and 4-fluoro-3-trifluoromethylbenzenesulfonylchloride as a light brown solid. MS (ESI$^-$): 464.4 ([M−H]$^-$).

Example 16

N-(1-Benzyl-3-oxo-2,3-dihydro-1H-indazol-5-yl)-2-chloro-5-trifluoromethyl-benzenesulfonamide This material was obtained in analogy to example 1 using 5-amino-1-benzyl-1,2-dihydro-indazol-3-one and 2-cloro-5-trifluoromethyl-benzenesulfonyl chloride as a light brown solid. MS (ESI$^-$): 480.3[M−H]$^-$).

Example 17

N-(1-Benzyl-3-oxo-2,3-dihydro-1H-indazol-5-yl)-3-phenoxy-benzenesulfonamide

This material was obtained in analogy to example 1 using 5-amino-1-benzyl-1,2-dihydro-indazol-3-one and 3-penoxy-benzenesulfonyl chloride as a light brown solid. MS (ESI$^-$): 470.3 [M−H]$^-$).

Example 18

N-(1-Benzyl-3-oxo-2,3-dihydro-1H-indazol-5-yl)-3-(5-methyl-[1,3,4]oxadiazol-2-yl)-benzenesulfonamide This material was obtained in analogy to example 1 using 5-amino-1-benzyl-1,2-dihydro-indazol-3-one and 3-(5-methyl-1,3,4-oxadiazol-2-yl)benzenesulfonyl chloride as a light brown solid. MS (ESI$^-$): 460.4[M−H]$^-$).

Example 19

N-(1-Benzyl-3-oxo-2,3-dihydro-1H-indazol-5-yl)-3-chloro-benzenesulfonamide

This material was obtained in analogy to example 1 using 5-amino-1-benzyl-1,2-dihydro-indazol-3-one and 3-chloro-benzenesulfonyl chloride as a light brown solid. MS (ESI$^-$): 412.1 [M−H]$^-$).

Example 20

N-(1-Benzyl-3-oxo-2,3-dihydro-1H-indazol-5-yl)-3-methoxy-benzenesulfonamide

This material was obtained in analogy to example 1 using 5-amino-1-benzyl-1,2-dihydro-indazol-3-one and 3-methoxy-benzenesulfonyl chloride as a light brown solid. MS (ESI$^-$): 408.0[M−H]$^-$).

Example 21

N-(1-Benzyl-3-oxo-2,3-dihydro-1H-indazol-5-yl)-3-difluoromethoxy-benzenesulfonamide This material was obtained in analogy to example 1 using 5-amino-1-benzyl-1,2-dihydro-indazol-3-one and 3-(difluoromethoxy)-benzenesulfonyl chloride as a colorless solid. MS (ESI$^-$): 444.1 [M−H]$^-$).

Example 22

N-(1-Benzyl-3-oxo-2,3-dihydro-1H-indazol-5-yl)-3,
5-bis-trifluoromethyl-benzenesulfonamide This compound was obtained in analogy to example 1 using 5-amino-1-benzyl-1,2-dihydro-indazol-3-one and 3,5-bistrifluoromethylbenzenesulfonyl chloride (step C) as a white solid. MS (ESI$^-$): 514.3 [M–H]$^-$).

Example 23

Propane-2-sulfonic acid (1-benzyl-3-oxo-2,3-dihydro-1H-indazol-5-yl)-amide

This compound was obtained in analogy to example 1 using 5-amino-1-benzyl-1,2-dihydro-indazol-3-one and 3 propane-2-sulfonyl chloride (step C) as a white solid. MS (ESI$^-$): 344.3 [M–H]$^-$).

Example 24

N-(1-Benzyl-3-oxo-2,3-dihydro-1H-indazol-5-yl)-3-chloro-2-N-dimethyl-benzenesulfonamide To a solution of NaH (0.005 g of a 60% dispersion in mineral oil) in DMF (2 mL) at 0° C. was added N-(1-benzyl-3-oxo-2,3-dihydro-1H-indazol-5-yl)-3-chloro-2-methyl-benzenesulfonamide in DMF (1 mL) dropwise. After 15 minutes MeI (0.017 g) was added and the reaction mixture was allowed to warm to ambient temperature. The reaction was quenched with water and diluted with EtOAc. The phases were separated and the aqueous phase was extracted with more EtOAc. The combined organic phases were washed with brine, dried over sodium sulfate, filtered and reduced in vacuo. Flash column chromatography over silica (EtOAc/nheptane) afforded the desired N-(1-benzyl-3-oxo-2,3-dihydro-1H-indazol-5-yl)-3-chloro-2-N-dimethyl-benzenesulfonamide as an off-white solid (13 mg). MS (ESI$^+$): 442.4 [M+H]$^+$).

Example 25

N-(3-Oxo-1-propyl-2,3-dihydro-1H-indazol-5-yl)-3-trifluoromethyl-benzenesulfonamide Step A] 1-Allyl-5-nitro-1,2-dihydro-indazol-3-one 5-Nitro-1,2-dihydro-indazol-3-one (prepared according to *Org. Synth.* 1949, 29, 54 or *Chem Ber.* 1942, 75, 1104) (9.36 g) was suspended in 40 ml water and 57.5 ml 1N KOH. Allyl bromide (6.32 g) was added in one portion. The mixture was stirred at 75-80° C. for 1.5 hours. Then NaOH (15%, 5 mL) and allyl bromide (1 g) was added. The reaction mixture was stirred for a further 30 min. The mixture was neutralized with 3N HCl at <10° C. and filtered. The solid was washed with water and dried. The solid was then suspended in 10 ml ethyl acetate and stirred at ambient temperature for 3 hours, then filtered and dried to afford the desired 1-allyl-5-nitro-1,2-dihydro-indazol-3-one (7.63 g) as a yellow solid.

Step B] 5-Amino-1-propyl-1,2-dihydro-indazol-3-one

Allyl-5-nitroindazolone (1.42 g) and Pd/C (10%, 250 mg) were suspended in MeOH (50 mL) and hydrogenated (hydrogen balloon) at RT for 4-5 h (or overnight.) After filtration and removal of MeOH, the solid was dried in vacuo to afford the desired 5-amino-1-propyl-1,2-dihydro-indazol-3-one (1.2 g) as a crude oil. This material was used in the next reaction without any further purification.

Step C] N-(3-Oxo-1-propyl-2,3-dihydro-1H-indazol-5-yl)-3-trifluoromethyl-benzenesulfonamide This material was obtained in analogy to example 1 using 5-amino-1-propyl-1,2-dihydro-indazol-3-one and 2,3-dichlorobenzenesulfonyl chloride.

Example 26

2,3-Dichloro-N-(3-oxo-1-propyl-2,3-dihydro-1H-indazol-5-yl)-benzenesulfonamide

This material was obtained in analogy to example 25 using 5-amino-1-propyl-1,2-dihydro-indazol-3-one and 2,3-dichlorobenzenesulfonyl chloride.

Example 27

Chloro-4-fluoro-N-(3-oxo-1-propyl-2,3-dihydro-1H-indazol-5-yl)-benzenesulfonamide This material was obtained in analogy to example 25 using 5-amino-1-propyl-1,2-dihydro-indazol-3-one and 3-chloro-4-fluoro-benzenesulfonyl chloride.

Example 28

Chloro-2-methyl-N-(3-oxo-1-phenethyl-2,3-dihydro-1H-indazol-5-yl)-benzenesulfonamide This compound was obtained in analogy to example 1 using phenethylhydrazine (step A) and 3-chloro-2-methyl-benzenesulfonyl chloride (step C) as a light yellow solid. MS (ESI$^+$): 442.3 [M+H]$^+$).

Example 29

Chloro-4-methyl-N-(3-oxo-1-phenethyl-2,3-dihydro-1H-indazol-5-yl)-benzenesulfonamide This compound was obtained in analogy to example 1 using phenethylhydrazine (step A) and 3-chloro-4-methyl-benzenesulfonyl chloride (step C) as a white solid. MS (ESI$^+$): 442.3 [M+H]$^+$).

Example 30

Chloro-2,5-dimethyl-N-(3-oxo-1-phenethyl-2,3-dihydro-1H-indazol-5-yl)-benzenesulfonamide This compound was obtained in analogy to example 1 using phenethylhydrazine (step A) and 4-chloro-2,5-dimethylbenzenesulfonyl chloride (step C) as a white solid. MS (ESI$^+$): 456.4[M+H]$^+$).

Example 31

N-(3-Oxo-1-phenethyl-2,3-dihydro-1H-indazol-5-yl)-3-trifluoromethyl-benzenesulfonamide This compound was obtained in analogy to example 1 using phenethylhydrazine (step A) and 3-trifluoromethylsulfonyl chloride (step C) as a red solid. MS (ESI$^+$): 462.1[M+H]$^+$).

Example 32

N-(1-Isobutyl-3-oxo-2,3-dihydro-1H-indazol-5-yl)-3-trifluoromethyl-benzenesulfonamide Step A] 1-Isobutyl-5-nitro-1,2-dihydro-indazol-3-one To a solution of 2-fluoro-5-nitrobenzoic acid (1.5 g) in DMF (50 mL) was added EDCI.HCl (1.71 g) followed by N-ethyldiisopropylamine (5.51 mL). After 10 minutes isobutylhydrazine.p-toluenesulfonicacid salt (2.32 g) was added. The reaction mixture was stirred at ambient temperature for 22 hours and the reaction was poured onto aqueous 1N HCl solution and extracted with EtOAc. The organic layer was washed with brine, dried over sodium sulfate, filtered and evaporated in vacuo. Purification via ISCO combiflash chromatography afforded pure desired 1-isobutyl-5-nitro-1,2-dihydro-indazol-3-one (0.9 g) as a yellow solid. MS (ESI$^-$): 234.1 ([M−H]$^-$).

Step B] 5-Amino-1-isobutyl-1,2-dihydro-indazol-3-one

To a solution of 1-isobutyl-5-nitro-1,2-dihydro-indazol-3-one (0.9 g) in MeOH (50 mL) was added Pd/C(10%) catalyst (0.3 g) and the reaction mixture was stirred for 1 hour at 40° C. under a hydrogen atmosphere using a balloon. After this time the reaction mixture was filtered through Celite® which was washed with more EtOAc. The combined organic solution was evaporated in vacuo for afford the desired 5-amino-1-isobutyl-1,2-dihydro-indazol-3-one (0.6 g) which was taken into the next reaction without further purification. MS (ESI$^+$): 206.1 ([M+H]$^+$).

Step C] N-(1-Isobutyl-3-oxo-2,3-dihydro-1H-indazol-5-yl)-3-trifluoromethyl-benzenesulfonamide To a solution of 5-amino-1-isobutyl-1,2-dihydro-indazol-3-one (0.04 g) in pyridine (1 mL) was added 3-trifluoromethylbenzenesulfonylchoride (0.041 g) in one go. The solution was stirred at 60° C. for 24 hours. The pyridine was then removed in vacuo and the residue was dissolved in EtOAc/water and separated. The aqueous phase was extracted a further two times with EtOAc and the combined organic phases were washed with brine and dried over sodium sulfate. The drying agent was removed by filtration and the volatiles were removed in vacuo to afford a crude residue. The crude material was purified via flash column chromatography eluting with EtOAc/nHeptane/1% AcOH) to afford the desired N-(1-isobutyl-3-oxo-2,3-dihydro-1H-indazol-5-yl)-3-trifluoromethyl-benzenesulfonamide (0.015 g) as a pale yellow powder. MS (ESI$^+$): 414.4[M+H]$^+$).

Example 33

3-Chloro-N-(1-isobutyl-3-oxo-2,3-dihydro-1H-indazol-5-yl)-4-methyl-benzenesulfonamide This compound was obtained in analogy to example 32 using 5-amino-1-isobutyl-1,2-dihydro-indazol-3-one and 3-chloro-4-methylbenzenesulfonyl chloride (step C) as a white solid. MS (ESI$^+$): 394.1[M+H]$^+$).

Example 34

3-Chloro-N-(1-isobutyl-3-oxo-2,3-dihydro-1H-indazol-5-yl)-2-methyl-benzenesulfonamide This compound was obtained in analogy to example 32 using 5-amino-1-isobutyl-1,2-dihydro-indazol-3-one and 3-chloro-2-methylbenzenesulfonyl chloride (step C) as a white solid. MS (ESI$^+$): 394.1 [M+H]$^+$).

Example 35

3-Cyano-(1-isobutyl-3-oxo-2,3-dihydro-indazol-5-yl)-benzenesulfonamide

This compound was obtained in analogy to example 32 using 5-amino-1-isobutyl-1,2-dihydro-indazol-3-one and 3-cyano-benzenesulfonyl chloride (step C) as an off-white solid. MS (ESI$^+$): 371.1 [M+H]$^+$).

Example 36

3-Difluoromethoxy-(1-isobutyl-3-oxo-2,3-dihydro—indazol-5-yl)-benzenesulfonamide This compound was obtained in analogy to example 32 using 5-amino-1-isobutyl-1,2-dihydro-indazol-3-one and 3-difluoromethoxy-benzenesulfonyl chloride (step C) as an off-white solid. MS (ESI$^+$): 412.4[M+H]$^+$).

Example 37

4-Cyano-(1-isobutyl-3-oxo-2,3-dihydro-indazol-5-yl)-benzenesulfonamide

This compound was obtained in analogy to example 32 using 5-amino-1-isobutyl-1,2-dihydro-indazol-3-one and 4-cyano-benzenesulfonyl chloride (step C) as an off-white solid. MS (ESI$^+$): 371.1 [M+H]$^+$).

Example 38

4-Fluoro-N-(1-isobutyl-3-oxo-2,3-dihydro-1H-indazol-5-yl)-3-trifluoromethyl-benzenesulfonamide This compound was obtained in analogy to example 32 using 5-amino-1-isobutyl-1,2-dihydro-indazol-3-one and 4-fluoro-3-trifluoromethylbenzenesulfonyl chloride (step C) as an off-white solid. MS (ESI$^+$): 432.4 [M+H]$^+$).

Example 39

3-Chloro-4-fluoro-N-(1-isobutyl-3-oxo-2,3-dihydro-1H-indazol-5-yl)-benzenesulfonamide This compound was obtained in analogy to example 32 using 5-amino-1-isobutyl-1,2-dihydro-indazol-3-one and 3-chloro-4-fluorobenzenesulfonyl chloride (step C) as an off-white solid. MS (ESI$^+$): 398.1 [M+H]$^+$).

Example 40

2,4-Dichloro-(1-isobutyl-3-oxo-2,3-dihydro-indazol-5-yl)-5-methyl-benzenesulfonamide This compound was obtained in analogy to example 32 using 5-amino-1-isobutyl-1,2-dihydro-indazol-3-one and 2,4-dimethyl-5-methylbenzenesulfonyl chloride (step C) as an orange solid. MS (ESI$^+$): 428.3 [M+H]$^+$).

Example 41

3-Chloro-N-(1-ethyl-3-oxo-2,3-dihydro-1H-indazol-5-yl)-2-methyl-benzenesulfonamide This compound was obtained in analogy to example 1 using ethylhydrazine.oxalate salt (step A) and 3-chloro-2-methylbenzenesulfonyl chloride (step C) as light yellow solid. MS (ESI$^+$): 366.0 [M+H]$^+$.

Example 42

3-Chloro-(1-cyclopropylmethyl-3-oxo-2,3-dihydro-indazol-5-yl)-2-methyl-benzenesulfonamide This compound was obtained in analogy to example 32 using cyclopropylmethyl-hydrazine (step A) (prepared as described in *J. Am. Chem. Soc.* 1986, 108, 7981-4) and 3-chloro-2-methylbenzenesulfonyl chloride (step C) as a light red solid. MS (ESI$^+$): 392.0 [M+H]$^+$.

Example 43

3-Chloro-(1-cyclopropylmethyl-3-oxo-2,3-dihydro-indazol-5-yl)-4-fluoro-benzenesulfonamide This compound was obtained in analogy to example 32 using cyclopropylmethyl-hydrazine (step A) (prepared as described in *J. Am. Chem. Soc.* 1986, 108, 7981-4) and 3-chloro-4-fluorobenzenesulfonyl chloride (step C) as a pink solid. MS (ESI$^+$): 396.3 [M+H]$^+$.

Example 44

Cyclopropylmethyl-3-oxo-2,3-dihydro-indazol-5-yl)-4-fluoro-3-trifluoromethyl-benzenesulfonamide This compound was obtained in analogy to example 32 using cyclopropylmethyl-hydrazine (step A) (prepared as described in *J. Am. Chem. Soc.* 1986, 108, 7981-4) and 4-fluoro-3-trifluoromethylbenzenesulfonyl chloride (step C) as a light red solid. MS (ESI$^+$): 430.4 [M+H]$^+$.

Example 45

3-Chloro-(1-cyclopropylmethyl-3-oxo-2,3-dihydro-indazol-5-yl)-benzenesulfonamide This compound was obtained in analogy to example 32 using cyclopropylmethyl-hydrazine (step A) (prepared as described in *J. Am. Chem. Soc.* 1986, 108, 7981-4) and 3-chlorobenzenesulfonyl chloride (step C) as an orange solid. MS (ESI$^+$): 378.3 [M+H]$^+$.

Example 46

2,4-Dichloro-(1-cyclopropylmethyl-3-oxo-2,3-dihydro-indazol-5-yl)-5-methyl-benzenesulfonamide This compound was obtained in analogy to example 32 using cyclopropylmethyl-hydrazine (step A) (prepared as described in *J. Am. Chem. Soc.* 1986, 108, 7981-4) and 2,4-dichloro-5-methylbenzenesulfonyl chloride (step C) as an orange solid. MS (ESI$^+$): 426.1 [M+H]$^+$.

Example 47

3-Chloro-[1-(2-methoxy-ethyl)-3-oxo-2,3-dihydro-indazol-5-yl]-2-methyl-benzenesulfonamide This compound was obtained in analogy to example 32 using (2-methoxy-ethyl)-hydrazine (step A) (prepared as described in *J. Org. Chem.* 1984, 49, 336-42) and 3-chloro-2-methylbenzenesulfonyl chloride (step C) as a white solid. MS (ESI$^+$): 396.3 [M+H]$^+$.

Example 48

4-Fluoro-[1-(2-methoxy-ethyl)-3-oxo-2,3-dihydro-indazol-5-yl]-3-trifluoromethyl-benzenesulfonamide This compound was obtained in analogy to example 32 using (2-methoxy-ethyl)-hydrazine (step A) (prepared as described in *J. Org. Chem.* 1984, 49, 336-42) and 4-fluoro-3-trifluoromethylbenzenesulfonyl chloride (step C) as a white solid. MS (ESI$^+$): 434.3 [M+H]$^+$.

Example 49

3-Chloro-4-fluoro-[1-(2-methoxy-ethyl)-3-oxo-2,3-dihydro-indazol-5-yl]-benzenesulfonamide This compound was obtained in analogy to example 32 using (2-methoxy-ethyl)-hydrazine (step A) (prepared as described in *J. Org. Chem.* 1984, 49, 336-42) and 3-chloro-4-fluorobenzenesulfonyl chloride (step C) as an off-white solid. MS (ESI$^+$): 400.3 [M+H]$^+$.

Example 50

2,4-Dichloro-[1-(2-methoxy-ethyl)-3-oxo-2,3-dihydro-indazol-5-yl]-6-methyl-benzenesulfonamide This compound was obtained in analogy to example 32 using (2-methoxy-ethyl)-hydrazine (step A) (prepared as described in *J. Org. Chem.* 1984, 49, 336-42) and 2,4-dichloro-6-methylbenzenesulfonyl chloride (step C) as a white solid. MS (ESI$^+$): 430.3 [M+H]$^+$.

Example 51

3-Chloro-2-methyl-N-[3-oxo-1-(2,2,2-trifluoro-ethyl)-2,3-dihydro-1H-indazol-5-yl]-benzene-sulfonamide This compound was obtained in analogy to example 32 using (2,2,2-trifluoro-ethyl)-hydrazine (step A) and 3-chloro-2-methylbenzenesulfonyl chloride (step C) as a red solid. MS (ESI$^+$): 420.3 [M+H]$^+$.

Example 52

4-Fluoro-[3-oxo-1-(2,2,2-trifluoro-ethyl)-2,3-dihydro-indazol-5-yl]-3-trifluoromethyl-benzenesulfonamide This compound was obtained in analogy to example 32 using (2,2,2-trifluoro-ethyl)-hydrazine (step A) and 4-fluoro-3-trifluoromethylbenzenesulfonyl chloride (step C) as a brown solid. MS (ESI$^+$): 458.4 [M+H]$^+$.

Example 53

4-Fluoro-N-(3-oxo-1-pyridin-2-ylmethyl-2,3-dihydro-1H-indazol-5-yl)-3-trifluoromethyl-benzenesulfonamide This compound was obtained in analogy to example 32 using pyridin-2-ylmethyl-hydrazine (step A) (prepared in analogy to examples described in *J. Org. Chem.* 1984, 49, 336-42) and 4-fluoro-3-trifluoromethylbenzenesulfonyl chloride (step C) as off-white solid. MS (ESI$^+$): 467.4 [M+H]$^+$).

Example 54

2,4-Dichloro-6-methyl-N-(3-oxo-1-pyridin-2-ylmethyl-2,3-dihydro-1H-indazol-5-yl)-benzenesulfonamide This compound was obtained in analogy to example 32 using pyridin-2-ylmethyl-hydrazine (step A) (prepared in analogy to examples described in *J. Org. Chem.* 1984, 49, 336-42) and 2,4-dichloro-6-methylbenzenesulfonyl chloride (step C) as off-white solid. MS (ESI$^+$): 463.3 [M+H]$^+$).

Example 55

3-Chloro-2-methyl-N-(3-oxo-1-pyridin-2-ylmethyl-2,3-dihydro-1H-indazol-5-yl)-benzenesulfonamide This compound was obtained in analogy to example 32 using pyridin-2-ylmethyl-hydrazine (step A) (prepared in analogy to examples described in *J. Org. Chem.* 1984, 49, 336-42) and 3-chloro-2-methylbenzenesulfonyl chloride (step C) as off-white solid. MS (ESI$^+$): 429.4 [M+H]$^+$).

Example 56

4-Fluoro-N-[1-(2-hydroxy-2-methyl-propyl)-3-oxo-2,3-dihydro-1H-indazol-5-yl]-3-trifluoromethyl-benzenesulfonamide This compound was obtained in analogy to example 32 using pyridin-2-ylmethyl-hydrazine (step A) (prepared as described in *Bioorg. Med. Chem.* 2004, 12, 1357-1366) and 4-fluoro-3-trifluoromethylbenzenesulfonyl chloride (step C) as off-white solid. MS (ESI$^+$): 448.3 [M+H]$^+$).

Example 57

N-(1-Benzyl-6-chloro-3-oxo-2,3-dihydro-1H-indazol-5-yl)-3-chloro-4-fluoro-benzenesulfonamide This compound was obtained in analogy to example 32 using 4-chloro-2-fluoro-5-nitro-benzoic acid, benzylhydrazine.2HCl (step A) and 3-chloro-4-fluorobenzenesulfonyl chloride (step C) as a light brown solid. MS (ESI$^-$): 464.1 [M−H]$^-$).

Example 58

N-(1-Benzyl-6-chloro-3-oxo-2,3-dihydro-1H-indazol-5-yl)-4-fluoro-3-trifluoromethyl-benzenesulfonamide This compound was obtained in analogy to example 32 using 4-chloro-2-fluoro-5-nitro-benzoic acid, benzylhydrazine.2HCl (step A) and 4-fluoro-3-trifluoromethylbenzenesulfonyl chloride (step C) as a light brown solid. MS (ESI$^-$): 498.0 [M−H]$^-$).

Example 59

N-(1-Benzyl-6-chloro-3-oxo-2,3-dihydro-1H-indazol-5-yl)-3-chloro-2-methyl-benzenesulfonamide This compound was obtained in analogy to example 32 using 4-chloro-2-fluoro-5-nitro-benzoic acid, benzylhydrazine.2HCl (step A) and 3-chloro-2-methylbenzenesulfonyl chloride (step C) as a light brown solid. MS (ESI$^-$): 460.0 [M−H]$^-$).

Example 60

N-(1-Benzyl-6-chloro-3-oxo-2,3-dihydro-1H-indazol-5-yl)-2,3-dichloro-benzenesulfonamide This compound was obtained in analogy to example 32 using 4-chloro-2-fluoro-5-nitro-benzoic acid, benzylhydrazine.2HCl (step A) and 2,3-dichloro-benzenesulfonyl chloride (step C) as a light brown solid. MS (ESI$^-$): 480.1 [M−H]$^-$).

Example 61

N-(1-Benzyl-6-chloro-3-oxo-2,3-dihydro-1H-indazol-5-yl)-3-cyano-benzenesulfonamide This compound was obtained in analogy to example 32 using 4-chloro-2-fluoro-5-nitro-benzoic acid, benzylhydrazine.2HCl (step A) and 3-cyano-benzenesulfonyl chloride (step C) as a light brown solid. MS (ESI$^-$): 437.0 [M−H]$^-$).

Example 62

N-(1-Benzyl-6-chloro-3-oxo-2,3-dihydro-1H-indazol-5-yl)-3-chloro-benzenesulfonamide This compound was obtained in analogy to example 32 using 4-chloro-2-fluoro-5-nitro-benzoic acid, benzylhydrazine.2HCl (step A) and 3-chloro-benzenesulfonyl chloride (step C) as a white solid. MS (ESI$^-$): 446.1 [M−H]$^-$).

Example 63

N-(1-Benzyl-6-chloro-3-oxo-2,3-dihydro-1H-indazol-5-yl)-4-chloro-3-trifluoromethyl-benzenesulfonamide This compound was obtained in analogy to example 32 using 4-chloro-2-fluoro-5-nitro-benzoic acid, benzylhydrazine.2HCl (step A) and 4-chloro-3-trifluoromethylbenzenesulfonyl chloride (step C) as a white solid. MS (ESI$^-$): 514.3 [M−H]$^-$).

Example 64

N-(1-Benzyl-6-chloro-3-oxo-2,3-dihydro-1H-indazol-5-yl)-3-difluoromethoxy-benzenesulfonamide This compound was obtained in analogy to example 32 using 4-chloro-2-fluoro-5-nitro-benzoic acid, benzylhydrazine.2HCl (step A) and 4-chloro-3-trifluoromethylbenzenesulfonyl chloride (step C) as a white solid. MS (ESI−): 478.0 [M−H]−).

Example 65

N-(1-Benzyl-6-chloro-3-oxo-2,3-dihydro-1H-indazol-5-yl)-2-trifluoromethyl-benzenesulfonamide This compound was obtained in analogy to example 32 using 4-chloro-2-fluoro-5-nitro-benzoic acid, benzylhydrazine.2HCl (step A) and 2-trifluoromethylbenzenesulfonyl chloride (step C) as a white solid. MS (ESI−): 480.0 [M−H]−).

Example 66

N-(1-Benzyl-6-chloro-3-oxo-2,3-dihydro-1H-indazol-5-yl)-3-trifluoromethoxy-benzenesulfonamide This compound was obtained in analogy to example 32 using 4-chloro-2-fluoro-5-nitro-benzoic acid, benzylhydrazine.2HCl (step A) and 3-trifluoromethoxybenzenesulfonyl chloride (step C) as a white solid. MS (ESI−): 496.4 [M−H]−).

Example 67

N-(1-Benzyl-6-chloro-3-oxo-2,3-dihydro-1H-indazol-5-yl)-2,5-difluoro-benzenesulfonamide This compound was obtained in analogy to example 32 using 4-chloro-2-fluoro-5-nitro-benzoic acid, benzylhydrazine.2HCl (step A) and 2,5-difluorobenzenesulfonyl chloride (step C) as a light red solid. MS (ESI−): 447.9 [M−H]−).

Example 68

N-(1-Benzyl-6-chloro-3-oxo-2,3-dihydro-1H-indazol-5-yl)-2,4-dichloro-benzenesulfonamide This compound was obtained in analogy to example 32 using 4-chloro-2-fluoro-5-nitro-benzoic acid, benzylhydrazine.2HCl (step A) and 2,4-dichlorobenzenesulfonyl chloride (step C) as a light brown solid. MS (ESI+): 482.4 [M+H]+).

Example 69

N-(1-Benzyl-6-chloro-3-oxo-2,3-dihydro-1H-indazol-5-yl)-3-chloro-2-fluoro-benzenesulfonamide This compound was obtained in analogy to example 32 using 4-chloro-2-fluoro-5-nitro-benzoic acid, benzylhydrazine.2HCl (step A) and 3-chloro-2-fluorobenzenesulfonyl chloride (step C) as a yellow solid. MS (ESI−): 464.1 [M−H]−).

Example 70

N-(1-Benzyl-6-chloro-3-oxo-2,3-dihydro-1H-indazol-5-yl)-3-trifluoromethyl-benzenesulfonamide This compound was obtained in analogy to example 32 using 4-chloro-2-fluoro-5-nitro-benzoic acid, benzylhydrazine.2HCl (step A) and 3-trifluoromethylbenzenesulfonyl chloride (step C) as a light red solid. MS (ESI−): 480.0 [M−H]−).

Example 71

N-(1-Benzyl-6-chloro-3-oxo-2,3-dihydro-1H-indazol-5-yl)-5-chloro-2-fluoro-benzenesulfonamide This compound was obtained in analogy to example 32 using 4-chloro-2-fluoro-5-nitro-benzoic acid, benzylhydrazine.2HCl (step A) and 3-chloro-6-fluorobenzenesulfonyl chloride (step C) as a brown solid. MS (ESI−): 464.1 [M−H]−).

Example 72

N-(1-Benzyl-6-chloro-3-oxo-2,3-dihydro-1H-indazol-5-yl)-2-chloro-benzenesulfonamide This compound was obtained in analogy to example 32 using 4-chloro-2-fluoro-5-nitro-benzoic acid, benzylhydrazine.2HCl (step A) and 2-chlorobenzenesulfonyl chloride (step C) as a light brown solid. MS (ESI−): 446.1 [M−H]−).

Example 73

Benzyl-4-chloro-3-oxo-2,3-dihydro-indazol-5-yl)-3-chloro-2-methyl-benzenesulfonamide This compound was obtained in analogy to example 32 using 2-chloro-6-fluoro-3-nitro-benzoic acid, benzylhydrazine.2HCl (step A) and 3-chloro-4-fluorobenzenesulfonyl chloride (step C) as a light brown solid. MS (ESI−): 460.1 [M−H]−).

Example 74

N-(1-Benzyl-6-fluoro-3-oxo-2,3-dihydro-1H-indazol-5-yl)-4-fluoro-3-trifluoromethyl-benzenesulfonamide This compound was obtained in analogy to example 32 using 2,4-difluoro-5-nitro-benzoic acid, benzylhydrazine.2HCl (step A) and 4-fluoro-3-trifluoromethylbenzenesulfonyl chloride (step C) as a light brown solid. MS (ESI+): 484.5 [M+H]+).

Example 75

N-(1-Benzyl-6-fluoro-3-oxo-2,3-dihydro-1H-indazol-5-yl)-2,3-dichloro-benzenesulfonamide This compound was obtained in analogy to example 32 using 2,4-difluoro-5-nitro-benzoic acid, benzylhydrazine.2HCl (step A) and 2,3-dichlorobenzenesulfonyl chloride (step C) as a light brown solid. MS (ESI−): 464.1 [M−H]−).

Example 76

N-(1-Benzyl-6-fluoro-3-oxo-2,3-dihydro-1H-indazol-5-yl)-2,4-dichloro-benzenesulfonamide This compound was obtained in analogy to example 32 using 2,4-difluoro-5-nitro-benzoic acid, benzylhydrazine.2HCl (step A) and 2,4-dichlorobenzenesulfonyl chloride (step C) as a light brown solid. MS (ESI$^-$): 464.1 [M−H]$^-$).

Example 77

N-(1-Benzyl-6-fluoro-3-oxo-2,3-dihydro-1H-indazol-5-yl)-3-chloro-2-fluoro-benzenesulfonamide This compound was obtained in analogy to example 32 using 2,4-difluoro-5-nitro-benzoic acid, benzylhydrazine.2HCl (step A) and 3-chloro-2-fluorobenzenesulfonyl chloride (step C) as a light brown solid. MS (ESI$^-$): 447.9 [M−H]$^-$).

Example 78

N-(1-Benzyl-6-fluoro-3-oxo-2,3-dihydro-1H-indazol-5-yl)-5-chloro-2-fluoro-benzenesulfonamide This compound was obtained in analogy to example 32 using 2,4-difluoro-5-nitro-benzoic acid, benzylhydrazine.2HCl (step A) and 3-chloro-6-fluorobenzenesulfonyl chloride (step C) as a light brown solid. MS (ESI$^-$): 447.9[M−H]$^-$).

Example 79

N-(1-Benzyl-6-fluoro-3-oxo-2,3-dihydro-1H-indazol-5-yl)-3-trifluoromethoxy-benzenesulfonamide This compound was obtained in analogy to example 32 using 2,4-difluoro-5-nitro-benzoic acid, benzylhydrazine.2HCl (step A) and 3-trifluoromethoxybenzenesulfonyl chloride (step C) as a light brown solid. MS (ESI$^+$): 482.4 [M+H]$^+$).

Example 80

3-Chloro-N-[1-(4-fluoro-benzyl)-3-oxo-2,3-dihydro-1H-indazol-5-yl]-benzenesulfonamide Step A] 1-(4-Fluoro-benzyl)-5-nitro-1,2-dihydro-indazol-3-one Nitro-1,2-dihydro-indazol-3-one (prepared according to *Org. Synth.* 1949, 29, 54 or *Chem Ber.* 1942, 75, 1104) (0.7 g) was suspended in 1 N NaOH (4.2 mL) and stirred for 10 minutes at 75° C. 4-Fluorobenzylbromide (0.48 mL) was then added dropwise over 2 hours. The reaction was stirred overnight and was quenched with 2 N HCl (aq.) solution while cooling in an ice bath. The precipitate was collected by filtration and the crude solid was either purified by flash column chromatography or by trituration with ether to give pure 1-(4-fluoro-benzyl)-5-nitro-1,2-dihydro-indazol-3-one. MS (ESI$^-$): 286.1 [M−H]$^-$).

Step B] 5-Amino-1-(4-fluoro-benzyl)-1,2-dihydro-indazol-3-one

To a solution of 1-(4-fluoro-benzyl)-5-nitro-1,2-dihydro-indazol-3-one (0.81 g) in MeOH (100 mL) was added Pd/C (10%) catalyst (0.1 g) and the reaction mixture was stirred for three hours at 40° C. under a hydrogen atmosphere using a balloon. After this time the reaction mixture was filtered through Celite® which was washed with more EtOAc. The combined organic solution was evaporated in vacuo for afford the desired 5-amino-1-(4-fluoro-benzyl)-1,2-dihydro-indazol-3-one (0.617 g) which was taken into the next reaction without further purification. MS (ESI$^+$): 258.3 ([M+H]$^+$).

Step C] 3-Chloro-N-[1-(4-fluoro-benzyl)-3-oxo-2,3-dihydro-1H-indazol-5-yl]-benzenesulfonamide To a solution of 5-amino-1-(4-fluoro-benzyl)-1,2-dihydro-indazol-3-one (0.100 g) in pyridine (1 mL) was added 3-chlorobenzenesulfonylchoride (0.082 g) in one go. The solution was stirred at 60° C. for 24 hours. The pyridine was then removed in vacuo and the residue was dissolved in EtOAc/water and separated. The aqueous phase was extracted a further two times with EtOAc and the combined organic phases were washed with brine and dried over sodium sulfate. The drying agent was removed by filtration and the volatiles were removed in vacuo to afford a crude residue. The crude material was purified via flash column chromatography eluting with EtOAc/nHeptane/1% AcOH) to afford the desired 3-chloro-N-[1-(4-fluoro-benzyl)-3-oxo-2,3-dihydro-1H-indazol-5-yl]-benzenesulfonamide (0.087 g) as a brown solid. MS (ESI$^+$): 432.4 [M+H]$^+$).

Example 81

3-Difluoromethoxy-N-[1-(4-fluoro-benzyl)-3-oxo-2,3-dihydro-1H-indazol-5-yl]-benzenesulfonamide This compound was obtained in analogy to example 80 using 5-amino-1-(4-fluoro-benzyl)-1,2-dihydro-indazol-3-one and 3-difluoromethoxybenzenesulfonyl chloride (step C) as a light brown solid. MS (ESI$^+$): 464.4 [M+H]$^+$).

Example 82

4-Fluoro-N-[1-(4-fluoro-benzyl)-3-oxo-2,3-dihydro-1H-indazol-5-yl]-3-trifluoromethyl-benzenesulfonamide This compound was obtained in analogy to example 80 using 5-amino-1-(4-fluoro-benzyl)-1,2-dihydro-indazol-3-one and 4-fluoro-3-trifluoromethylbenzenesulfonyl chloride (step C) as a light brown solid. MS (ESI$^-$): 482.3 [M−H]$^-$).

Example 83

2,3-Dihydro-benzo[1,4]dioxine-6-sulfonic acid [1-(4-fluoro-benzyl)-3-oxo-2,3-dihydro-1H-indazol-5-yl]-amide This compound was obtained in analogy to example 80 using 5-amino-1-(4-fluoro-benzyl)-1,2-dihydro-indazol-3-one and 3-dihydro-1,4-benzodioxine-6-sulfonyl chloride (step C) as a light brown solid. MS (ESI$^-$): 456.5 [M−H]$^-$).

Example 84

2,4-Dichloro-N-[1-(4-fluoro-benzyl)-3-oxo-2,3-dihydro-1H-indazol-5-yl]-6-methyl-benzenesulfonamide This compound was obtained in analogy to example 80 using 5-amino-1-(4-fluoro-benzyl)-1,2-dihydro-indazol-3-one and 2,4-dichloro-6-methylbenzenesulfonyl chloride (step C) as a light brown solid. MS (ESI$^+$): 480.4 [M+H]$^+$).

Example 85

5-Chloro-2,4-difluoro-N-[1-(4-fluoro-benzyl)-3-oxo-2,3-dihydro-1H-indazol-5-yl]-benzenesulfonamide This compound was obtained in analogy to example 80 using 5-amino-1-(4-fluoro-benzyl)-1,2-dihydro-indazol-3-one and 3-chloro-4,6-difluorobenzenesulfonyl chloride (step C) as an off-white solid. MS (ESI$^+$): 468.4 [M+H]$^+$).

Example 86

4-Chloro-2,5-difluoro-N-[1-(4-fluoro-benzyl)-3-oxo-2,3-dihydro-1H-indazol-5-yl]-benzenesulfonamide This compound was obtained in analogy to example 80 using 5-amino-1-(4-fluoro-benzyl)-1,2-dihydro-indazol-3-one and 4-chloro-2,5-difluorobenzenesulfonyl chloride (step C) as an off-white solid. MS (ESI$^+$): 468.4 [M+H]$^+$).

Example 87

3-Chloro—[1-(4-fluoro-benzyl)-3-oxo-2,3-dihydro-indazol-5-yl]-2-methyl-benzenesulfonamide This compound was obtained in analogy to example 80 using 5-amino-1-(4-fluoro-benzyl)-1,2-dihydro-indazol-3-one and 3-chloro-2-methylbenzenesulfonyl chloride (step C) as an off-white solid. MS (ESI$^+$): 446.0 [M+H]$^+$).

Example 88

3-Cyano-[1-(4-fluoro-benzyl)-3-oxo-2,3-dihydro-indazol-5-yl]-benzenesulfonamide

This compound was obtained in analogy to example 80 using 5-amino-1-(4-fluoro-benzyl)-1,2-dihydro-indazol-3-one and 3-cyanobenzenesulfonyl chloride (step C) as light brown solid. MS (ESI$^+$): 423.1 [M+H]$^+$).

Example 89

Naphthalene-1-sulfonic acid [1-(4-fluoro-benzyl)-3-oxo-2,3-dihydro-1H-indazol-5-yl]-amide This compound was obtained in analogy to example 80 using 5-amino-1-(4-fluoro-benzyl)-1,2-dihydro-indazol-3-one and 1-naphthalenesulfonyl chloride (step C) as light brown solid. MS (ESI$^+$): 448.3 [M+H]$^+$).

Example 90

3-Chloro-4-fluoro-N-[1-(4-fluoro-benzyl)-3-oxo-2,3-dihydro-1H-indazol-5-yl]-benzenesulfonamide This compound was obtained in analogy to example 80 using 5-amino-1-(4-fluoro-benzyl)-1,2-dihydro-indazol-3-one and 3-chloro-4-fluorobenzenesulfonyl chloride (step C) as light brown foam. MS (ESI$^+$): 449.9 [M+H]$^+$).

Example 91

3-Chloro-[1-(3,4-difluoro-benzyl)-3-oxo-2,3-dihydro-indazol-5-yl]-2-methyl-benzenesulfonamide This compound was obtained in analogy to example 80 using 3,4-difluorobenzylbromide (step A) and 3-chloro-2-methylbenzenesulfonyl chloride (step C) as a white solid. MS (ESI$^+$): 464.3 [M+H]$^+$).

Example 92

3-Chloro-[1-(3,4-difluoro-benzyl)-3-oxo-2,3-dihydro-indazol-5-yl]-4-fluoro-benzenesulfonamide This compound was obtained in analogy to example 80 using 3,4-difluorobenzylbromide (step A) and 3-chloro-4-fluorobenzenesulfonyl chloride (step C) as a white solid. MS (ESI$^+$): 468.4 [M+H]$^+$).

Example 93

[1-(3,4-Difluoro-benzyl)-3-oxo-2,3-dihydro-indazol-5-yl]-4-fluoro-3-trifluoromethyl-benzenesulfonamide This compound was obtained in analogy to example 80 using 3,4-difluorobenzylbromide (step A) and 4-fluoro-3-trifluoromethylbenzenesulfonyl chloride (step C) as a white solid. MS (ESI$^+$): 502.1 [M+H]$^+$).

Example 94

3-Chloro-[1-(3,4-difluoro-benzyl)-3-oxo-2,3-dihydro-indazol-5-yl]-benzenesulfonamide This compound was obtained in analogy to example 80 using 3,4-difluorobenzylbromide (step A) and 3-chlorobenzenesulfonyl chloride (step C) as an orange solid. MS (ESI$^+$): 450.3 [M+H]$^+$).

Example 95

[1-(3,4-Difluoro-benzyl)-3-oxo-2,3-dihydro-indazol-5-yl]-3-trifluoromethoxy-benzenesulfonamide This compound was obtained in analogy to example 80 using 3,4-difluorobenzylbromide (step A) and 3-trifluoromethoxybenzenesulfonyl chloride (step C) as a white solid. MS (ESI$^+$): 500.3 [M+H]$^+$).

Example 96

2,4-Dichloro-[1-(3,4-difluoro-benzyl)-3-oxo-2,3-dihydro-indazol-5-yl]-5-methyl-benzenesulfonamide This compound was obtained in analogy to example 80 using 3,4-difluorobenzylbromide (step A) and 2,4-dichloro-5-methylbenzenesulfonyl chloride (step C) as a white solid. MS (ESI$^+$): 498.4 [M+H]$^+$).

Example 97

3,4-Dichloro-[1-(3,4-difluoro-benzyl)-3-oxo-2,3-dihydro-indazol-5-yl]-benzenesulfonamide This compound was obtained in analogy to example 80 using 3,4-difluorobenzylbromide (step A) and 3,4-dichlorobenzenesulfonyl chloride (step C) as a white solid. MS (ESI$^+$): 484.4 [M+H]$^+$).

Example 98

4,5-Dichloro-[1-(3,4-difluoro-benzyl)-3-oxo-2,3-dihydro-indazol-5-yl]-2-fluoro-benzenesulfonamide This compound was obtained in analogy to example 80 using 3,4-difluorobenzylbromide (step A) and 3,4-dichloro-6-fluorobenzenesulfonyl chloride (step C) as a white solid. MS (ESI$^+$): 502.1 [M+H]$^+$).

Example 99

2,4,5-Trichloro-[1-(3,4-difluoro-benzyl)-3-oxo-2,3-dihydro-indazol-5-yl]-benzenesulfonamide This compound was obtained in analogy to example 80 using 3,4-difluorobenzylbromide (step A) and 3,4,6-trichloro-benzenesulfonyl chloride (step C) as a white solid. MS (ESI$^+$): 520.3 [M+H]$^+$).

Example 100

2,3-Dichloro-[1-(3,4-difluoro-benzyl)-3-oxo-2,3-dihydro-indazol-5-yl]-6-methyl-benzenesulfonamide This compound was obtained in analogy to example 80 using 3,4-difluorobenzylbromide (step A) and 2,3-dichlorobenzenesulfonyl chloride (step C) as a white solid. MS (ESI$^+$): 484.4 [M+H]$^+$).

Example 101

2,4-Dichloro-[1-(3,4-difluoro-benzyl)-3-oxo-2,3-dihydro-indazol-5-yl]-6-methyl-benzenesulfonamide This compound was obtained in analogy to example 80 using 3,4-difluorobenzylbromide (step A) and 2,4-dichloro-6-methylbenzenesulfonyl chloride (step C) as a white solid. MS (ESI$^+$): 500.3 [M+H]$^+$).

Example 102

3-Chloro-N-[1-(2,4-difluoro-benzyl)-3-oxo-2,3-dihydro-1H-indazol-5-yl]-4-fluoro-benzenesulfonamide This compound was obtained in analogy to example 80 using 2,4-difluorobenzylbromide (step A) and 3-chloro-4-fluorobenzenesulfonyl chloride (step C) as a pink solid. MS (ESI$^+$): 468.4 [M+H]$^+$).

Example 103

N-[1-(2,4-Difluoro-benzyl)-3-oxo-2,3-dihydro-1H-indazol-5-yl]-4-fluoro-3-trifluoromethyl-benzenesulfonamide This compound was obtained in analogy to example 80 using 2,4-difluorobenzylbromide (step A) and 4-fluoro-3-trifluoromethylbenzenesulfonyl chloride (step C) as a white solid. MS (ESI$^+$): 502.1 [M+H]$^+$).

Example 104

3-Chloro-N-[1-(2,4-difluoro-benzyl)-3-oxo-2,3-dihydro-1H-indazol-5-yl]-2-methyl-benzenesulfonamide This compound was obtained in analogy to example 80 using 2,4-difluorobenzylbromide (step A) and 3-chloro-2-methylbenzenesulfonyl chloride (step C) as a white solid. MS (ESI$^+$): 464.3 [M+H]$^+$).

Example 105

N-[1-(4-Chloro-benzyl)-3-oxo-2,3-dihydro-1H-indazol-5-yl]-4-fluoro-3-trifluoromethyl-benzenesulfonamide Step A] 1-(4-Chloro-benzyl)-5-nitro-1,2-dihydro-indazol-3-one This compound was obtained in analogy to step A in example 77 using 5-nitro-1,2-dihydro-indazol-3-one (prepared according to *Org. Synth.* 1949, 29, 54 or *Chem Ber.* 1942, 75, 1104) and 4-chlorobenzylbromide to afford the desired 1-(4-chloro-benzyl)-5-nitro-1,2-dihydro-indazol-3-one as a brown solid. MS (ESI$^-$): 302.3 [M–H]$^-$).

Step B] 5-Amino-1-(4-chloro-benzyl)-1,2-dihydro-indazol-3-one

To 1-(4-chloro-benzyl)-5-nitro-1,2-dihydro-indazol-3-one (0.45 g) was added HCl (37% aq.) solution (5 mL) followed by SnCl$_2$.dihydrate (1.9 g). The mixture was heated to 85° C. for one hour. The reaction was then neutralized with sodium bicarbonate solution, filtered, and the filtrate extracted with EtOAc. The combined organic phases were washed with brine, dried over sodium sulfate, filtered and reduced in vacuo. Flash column chromatography of the residue over silica gel eluting with methylene chloride/methanol afforded the desired 5-amino-1-(4-chloro-benzyl)-1,2-dihydro-indazol-3-one (0.31 g) as a dark brown solid. MS (ESI$^+$): 274.4 [M+H]$^+$).

Step C] N-[1-(4-Chloro-benzyl)-3-oxo-2,3-dihydro-1H-indazol-5-yl]-4-fluoro-3-trifluoromethyl-benzenesulfonamide This compound was obtained in analogy to step C in example 77 using 4-fluoro-3-trifluoromethylbenzenesulfonyl chloride (step C) as a white solid. MS (ESI$^+$): 500.3 [M+H]$^+$).

Example 106

3-Chloro-N-[1-(4-chloro-benzyl)-3-oxo-2,3-dihydro-1H-indazol-5-yl]-2-methyl-benzenesulfonamide This compound was obtained in analogy to example 105 using 5-amino-1-(4-chloro-benzyl)-1,2-dihydro-indazol-3-one and 3-chloro-2-methylbenzenesulfonyl chloride (step C) as a light brown solid. MS (ESI$^+$): 462.1 [M+H]$^+$).

Example 107

2,3-Dichloro-N-[1-(4-chloro-benzyl)-3-oxo-2,3-dihydro-1H-indazol-5-yl]-benzenesulfonamide This compound was obtained in analogy to example 105 using 5-amino-1-(4-chloro-benzyl)-1,2-dihydro-indazol-3-one and 2,3-dichlorobenzenesulfonyl chloride (step C) as a light brown solid. MS (ESI$^+$): 482.4 [M+H]$^+$).

Example 108

Naphthalene-1-sulfonic acid [1-(4-chloro-benzyl)-3-oxo-2,3-dihydro-1H-indazol-5-yl]-amide This compound was obtained in analogy to example 105 using 5-amino-1-(4-chloro-benzyl)-1,2-dihydro-indazol-3-one and 1-naphthalenesulfonyl chloride (step C) as an off-white solid. MS (ESI$^+$): 464.1 [M+H]$^+$).

Example 109

3-Chloro-N-[1-(2-chloro-4-fluoro-benzyl)-3-oxo-2,3-dihydro-1H-indazol-5-yl]-2-methyl-benzenesulfonamide This compound was obtained in analogy to example 105 using 2-chloro-4-fluorobenzylbromide (step A) and 3-chloro-2-methylbenzenesulfonyl chloride (step C) as a light brown solid. MS (ESI$^+$): 480.4 [M+H]$^+$).

Example 110

Naphthalene-1-sulfonic acid [1-(2-chloro-4-fluoro-benzyl)-3-oxo-2,3-dihydro-1H-indazol-5-yl]-amide This compound was obtained in analogy to example 105 using 2-chloro-4-fluorobenzylbromide (step A) and 1-naphthalenesulfonyl chloride (step C) as a light brown solid. MS (ESI$^+$): 482.4 [M+H]$^+$).

Example 111

2,3-Dichloro-N-[1-(2-chloro-4-fluoro-benzyl)-3-oxo-2,3-dihydro-1H-indazol-5-yl]-benzenesulfonamide This compound was obtained in analogy to example 105 using 2-chloro-4-fluorobenzylbromide (step A) and 2,3-dichlorobenzenesulfonyl chloride (step C) as a light brown solid. MS (ESI$^+$): 500.1 [M+H]$^+$).

Example 112

N-[1-(2-Chloro-4-fluoro-benzyl)-3-oxo-2,3-dihydro-1H-indazol-5-yl]-4-fluoro-3-trifluoromethyl-benzenesulfonamide This compound was obtained in analogy to example 105 using 2-chloro-4-fluorobenzylbromide (step A) and 4-fluoro-3-trifluoromethylbenzenesulfonyl chloride (step C) as an off-white solid. MS (ESI$^-$): 516.2 [M−H]$^-$).

Example 113

N-[1-(2-Chloro-4-fluoro-benzyl)-3-oxo-2,3-dihydro-1H-indazol-5-yl]-3-difluoromethoxy-benzenesulfonamide This compound was obtained in analogy to example 105 using 2-chloro-4-fluorobenzylbromide (step A) and 3-difluoromethoxybenzenesulfonyl chloride (step C) as a light brown solid. MS (ESI$^-$): 496.3 [M−H]$^-$).

Example 114

N-[1-(2-Chloro-4-fluoro-benzyl)-3-oxo-2,3-dihydro-1H-indazol-5-yl]-3-trifluoromethoxy-benzenesulfonamide This compound was obtained in analogy to example 105 using 2-chloro-4-fluorobenzylbromide (step A) and 3-trifluoromethoxybenzenesulfonyl chloride (step C) as an off-white solid. MS (ESI$^-$): 514.3 [M−H]$^-$).

Example 115

3-Chloro-N-[1-(2-cyano-ethyl)-3-oxo-2,3-dihydro-1H-indazol-5-yl]-2-methyl-benzenesulfonamide Step A] 3-(5-Nitro-3-oxo-2,3-dihydro-indazol-1-yl)-propionitrile 5-Nitro-1,2-dihydro-indazol-3-one (prepared according to *Org. Synth.* 1949, 29, 54 or *Chem Ber.* 1942, 75, 1104) (0.6 g) was suspended in water (8 mL) and 2N K$_2$CO$_3$ (aq.) (1.8 g) was added to the flask and the mixture was heated to 50° C. for 10 minutes. Acrylonitrile (0.24 mL) was then added dropwise. The reaction was stirred overnight and was quenched with 2 N HCl (aq.) solution while cooling in an ice bath. The aqueous phase was extracted with EtOAc and the combined phases were washed with brine, dried over sodium sulfate, filtered and reduced in vacuo. Flash column chromatography over silica gel (eluting with EtOAc, nheptane, 3% AcOH) afforded pure desired 3-(5-Nitro-3-oxo-2,3-dihydro-indazol-1-yl)-propionitrile as a white solid. MS (ESI$^+$: 233.3[M+H]$^+$).

Step B] 3-(5-Amino-3-oxo-2,3-dihydro-indazol-1-yl)-propionitrile

To a solution of 3-(5-Nitro-3-oxo-2,3-dihydro-indazol-1-yl)-propionitrile (0.521 g) in MeOH (50 mL) was added Pd/C (10%) catalyst (0.13 g) and the reaction mixture was stirred for 20 hours at ambient temperature under a hydrogen atmosphere using a balloon. After this time the reaction mixture was filtered through Celite® which was washed with more EtOAc. The combined organic solution was evaporated in vacuo for afford the desired 3-(5-amino-3-oxo-2,3-dihydro-indazol-1-yl)-propionitrile (0.45 g) which was taken into the next reaction without further purification. MS (ESI$^+$): 203.4 ([M+H]$^+$).

Step C] 3-Chloro-N-[1-(2-cyano-ethyl)-3-oxo-2,3-dihydro-1H-indazol-5-yl]-2-methyl-benzenesulfonamide To a solution of 3-(5-amino-3-oxo-2,3-dihydro-indazol-1-yl)-propionitrile (0.08 g) in pyridine (1 mL) was added 3-chloro-2-methylbenzenesulfonylchoride (0.089 g) in one go. The solution was stirred at 60° C. for 24 hours. The pyridine was then removed in vacuo and the residue was dissolved in EtOAc/water and separated. The aqueous phase was extracted a further two times with EtOAc and the combined organic phases were washed with brine and dried over sodium sulfate. The drying agent was removed by filtration and the volatiles were removed in vacuo to afford a crude residue. The crude material was purified via flash column chromatography eluting with EtOAc/nHeptane/1% AcOH) to afford the desired 3-Chloro-N-[1-(2-cyano-ethyl)-3-oxo-2,3-dihydro-1H-indazol-5-yl]-2-methyl-benzenesulfonamide (0.087 g) as a light brown solid. MS (ESI$^+$): 391.0 [M+H]$^+$).

Example 116

N-[1-(2-Cyano-ethyl)-3-oxo-2,3-dihydro-1H-indazol-5-yl]-4-fluoro-3-trifluoromethylbenzenesulfonamide This compound was obtained in analogy to example 115 using 3-(5-amino-3-oxo-2,3-dihydro-indazol-1-yl)-propionitrile and 4-fluoro-3-trifluoromethylbenzenesulfonyl chloride (step C) as a white solid. MS (ESI$^+$): 429.5 [M+H]$^+$).

Example 117

2,4-Dichloro-N-[1-(2-cyano-ethyl)-3-oxo-2,3-dihydro-1H-indazol-5-yl]-6-methyl-benzenesulfonamide This compound was obtained in analogy to example 115 using 3-(5-amino-3-oxo-2,3-dihydro-indazol-1-yl)-propionitrile and 2,4-dichloro-6-methylbenzenesulfonyl chloride (step C) as a light red solid. MS (ESI$^+$): 425.3 [M+H]$^+$).

Example 118

3-Chloro-N-[1-(2-cyano-ethyl)-3-oxo-2,3-dihydro-1H-indazol-5-yl]-4-fluoro-benzenesulfonamide This compound was obtained in analogy to example 115 using 3-(5-amino-3-oxo-2,3-dihydro-indazol-1-yl)-propionitrile and 3-chloro-4-fluorobenzenesulfonyl chloride (step C) as a light red solid. MS (ESI$^+$): 395.3 [M+H]$^+$).

Example 119

N-[6-Chloro-1-(2-chloro-benzyl)-3-oxo-2,3-dihydro-1H-indazol-5-yl]-4-fluoro-3-trifluoromethyl-benzenesulfonamide Step A] 6-Chloro-1-(2-chloro-benzyl)-5-nitro-1,2-dihydro-indazol-3-one Chloro-5-nitro-1,2-dihydro-indazol-3-one (prepared in analogy to *Org. Synth.* 1949, 29, 54 or *Chem Ber.* 1942, 75, 1104 from 4-chloro-2-fluoro-5-nitro-benzoic acid over two steps) (0.6 g) was suspended in water (5 mL) and 2N $K_2CO_3$ (aq.) (1 g) was added to the flask and the mixture was heated to 50° C. for 10 minutes. 2-Chlorobenzylbromide (0.40 g) was then added dropwise. The reaction was stirred overnight and was neutralized with 2 N HCl (aq.) while cooling in an ice bath. The precipitate was collected by filtration and triturated with diethylether to afford pure desired 6-chloro-1-(2-chloro-benzyl)-5-nitro-1,2-dihydro-indazol-3-one as a brown solid. MS (ESI$^-$:336.3[M−H]$^-$).

Step B] 5-Amino-6-chloro-1-(2-chloro-benzyl)-1,2-dihydro-indazol-3-one

To 6-chloro-1-(2-chloro-benzyl)-5-nitro-1,2-dihydro-indazol-3-one (0.49 g) was added HCl (37% aq.) solution (4 mL) followed by $SnCl_2$.dihydrate (2.6 g). The mixture was heated to 85° C. for one hour. The reaction was then neutralized with sodium bicarbonate solution, filtered, and the filtrate extracted with EtOAc. The combined organic phases were washed with brine, dried over sodium sulfate, filtered and reduced in vacuo. Flash column chromatography of the residue over silica gel eluting with methylene chloride/methanol afforded the desired 5-amino-6-chloro-1-(2-chloro-benzyl)-1,2-dihydro-indazol-3-one (0.33 g) as a yellow solid. MS (ESI$^+$): 308.3 [M+H]$^+$).

Step C] N-[6-Chloro-1-(2-chloro-benzyl)-3-oxo-2,3-dihydro-1H-indazol-5-yl]-4-fluoro-3-trifluoromethyl-benzenesulfonamide To a solution of 5-amino-6-chloro-1-(2-chloro-benzyl)-1,2-dihydro-indazol-3-one (0.070 g) in pyridine (1 mL) was added f-fluoro-3-trifluoromethylbenzenesulfonylchoride (0.072 g) in one go. The solution was stirred at 60° C. for 24 hours. The pyridine was then removed in vacuo and the residue was dissolved in EtOAc/water and separated. The aqueous phase was extracted a further two times with EtOAc and the combined organic phases were washed with brine and dried over sodium sulfate. The drying agent was removed by filtration and the volatiles were removed in vacuo to afford a crude residue. The crude material was purified via flash column chromatography eluting with EtOAc/nHeptane/1% AcOH) to afford the desired N-[6-chloro-1-(2-chloro-benzyl)-3-oxo-2,3-dihydro-1H-indazol-5-yl]-4-fluoro-3-trifluoromethyl-benzenesulfonamide (0.024 g) as a light brown solid. MS (ESI$^+$): 534.3 [M+H]$^+$).

Example 120

5-Chloro-N-[6-chloro-1-(2-chloro-benzyl)-3-oxo-2,3-dihydro-1H-indazol-5-yl]-2-fluoro-benzenesulfonamide This compound was obtained in analogy to example 119 using 5-amino-6-chloro-1-(2-chloro-benzyl)-1,2-dihydro-indazol-3-one and 3-chloro-6-fluorobenzenesulfonyl chloride (step C) as a light brown solid. MS (ESI$^+$): 500.3 [M+H]$^+$).

Example 121

2,3-Dichloro-N-[6-chloro-1-(2-chloro-benzyl)-3-oxo-2,3-dihydro-1H-indazol-5-yl]-benzenesulfonamide This compound was obtained in analogy to example 119 using 5-amino-6-chloro-1-(2-chloro-benzyl)-1,2-dihydro-indazol-3-one and 2,3-dichlorobenzenesulfonyl chloride (step C) as a light brown solid. MS (ESI$^+$): 518.0 [M+H]$^+$).

Example 122

3-Chloro-N-(6-chloro-3-oxo-1-pyridin-2-ylmethyl-2,3-dihydro-1H-indazol-5-yl)-2-methyl-benzenesulfonamide This compound was obtained in analogy to example 119 using 2-chloromethyl-pyridine (step A) and 3-chloro-2-methylbenzenesulfonyl chloride (step C) as an off-white solid. MS (ESI$^+$): 463.1 [M+H]$^+$).

Example 123

N-(6-Chloro-3-oxo-1-pyridin-2-ylmethyl-2,3-dihydro-1H-indazol-5-yl)-4-fluoro-3-trifluoromethyl-benzenesulfonamide This compound was obtained in analogy to example 119 using 2-chloromethyl-pyridine (step A) and 4-fluoro-3-trifluoromethylbenzenesulfonyl chloride (step C) as a white solid. MS (ESI$^+$): 501.4[M+H]$^+$).

Example 124

2-[5-(3-Chloro-2-methyl-benzenesulfonylamino)-3-oxo-2,3-dihydro-indazol-1-yl]-methyl-acetamide Part A] (5-Nitro-3-oxo-2,3-dihydro-indazol-1-yl)-acetic acid ethyl ester This compound was obtained in analogy to example 1 (step A) using hydrazino-acetic acid ethyl ester.HCl as an orange solid. MS (ESI$^-$): 264.1[M−H]$^-$).

Part B] (5-Nitro-3-oxo-2,3-dihydro-indazol-1-yl)-acetic acid

To a solution of (5-nitro-3-oxo-2,3-dihydro-indazol-1-yl)-acetic acid ethyl ester (0.24 g) in THF (9 mL), was added 2 N NaOH (aq.) (1.8 mL). The reaction mixture was stirred at ambient temperature for 30 minutes. The reaction mixture was acidified with 2 N HCl (aq.) and extricated with EtOAc. Evaporation of the organic phases afforded the desired crude (5-nitro-3-oxo-2,3-dihydro-indazol-1-yl)-acetic acid (0.146 g) which was taken into the next step without further purification.

Part C] N-Methyl-2-(5-nitro-3-oxo-2,3-dihydro-indazol-1-yl)-acetamide

To a solution of crude (5-nitro-3-oxo-2,3-dihydro-indazol-1-yl)-acetic acid (0.14 g) in DMF, was added TBTU (0.20 g), followed by N,N-ethyldiisopropylamine (0.40 mL) and after 10 minutes methylamine (0.32 mL of a 2 M solution) was added. The reaction was stirred overnight and was quenched with 2N HCl (aq.) and extracted with EtOAc. The combined organic layers were washed with brine, dried over sodium sulfate, filtered and evaporated. Flash column chromatography of the residue over silica gel afforded the desired N-methyl-2-(5-nitro-3-oxo-2,3-dihydro-indazol-1-yl)-acetamide (0.040 g) as a yellow solid. MS (ESI$^-$):249.1 ([M−H]$^-$).

Part D and E] 2-[5-(3-Chloro-2-methyl-benzenesulfonylamino)-3-oxo-2,3-dihydro-indazol-1-yl]-methyl-acetamide This compound was obtained in analogy to example 1 (step B and C) using 3-chloro-2-methylbenzenesulfonyl chloride (step C) as an off-white solid. MS (ESI$^+$): 409.1 [M+H]$^+$).

Example 125

2,4-Dichloro-[1-(3,4-difluoro-benzyl)-2-methyl-3-oxo-2,3-dihydro-indazol-5-yl]-6-methyl-benzenesulfonamide Part A] 1-(3,4-Difluoro-benzyl)-2-methyl-5-nitro-1,2-dihydro-indazol-3-one To a solution of 1-(3,4-difluoro-benzyl)-5-nitro-1,2-dihydro-indazol-3-one (prepared in analogy to example 80 using 3,4-difluorobenzylbromide (step A)) (0.2 g) in DMF was added NaH (0.019 g) and the solution was stirred for 1 hour. Iodomethane (0.14 g) was then added and the mixture was stirred overnight. The reaction mixture was quenched with water and extracted with EtOAc. The combined organic layers were washed with brine, dried over sodium sulfate, filtered and evaporated in vacuo to afford a crude orange residue. Flash column chromatography of the crude residue over silica gel afforded the desired 1-(3,4-difluoro-benzyl)-2-methyl-5-nitro-1,2-dihydro-indazol-3-one (0.11 g) as a yellow solid. MS (ESI$^-$): 318.1 ([M−H]$^-$).

Part B] 12,4-Dichloro-[1-(3,4-difluoro-benzyl)-2-methyl-3-oxo-2,3-dihydro-indazol-5-yl]-6-methyl-benzenesulfonamide This compound was obtained in analogy to example 1 (step B and C) using 2,4-dichloro-6-methylbenzenesulfonyl chloride (step C) as a white solid. MS (ESI$^+$): 534.2 [M+Na]$^+$).

Example 126

3-Chloro-[1-(3,4-difluoro-benzyl)-2-methyl-3-oxo-2,3-dihydro-indazol-5-yl]-2-methyl-benzenesulfonamide This compound was obtained in analogy to example 125 using 3-chloro-2-methylbenzenesulfonyl chloride (step C) as a white solid. MS (ESI$^-$): 478.3 [M−H]$^-$).

Example 127

2,3-Dichloro-N-(6-chloro-3-oxo-1-pyridin-2-ylmethyl-2,3-dihydro-1H-indazol-5-yl)-benzenesulfonamide This compound was obtained in analogy to example 119 using 2-chloromethyl-pyridine (step A) and 2,3-dichlorobenzenesulfonyl chloride (step C) as a light brown solid. MS (ESI$^+$): 482.9[M+H]$^+$).

Example 128

N-(1-Benzyl-6-fluoro-3-oxo-2,3-dihydro-1H-indazol-5-yl)-2,4-difluoro-benzenesulfonamide This compound was obtained in analogy to example 32 using 2,4-difluoro-5-nitro-benzoic acid, benzylhydrazine.2HCl (step A) and 2,4-difluorobenzenesulfonyl chloride (step C) as a light brown solid. MS (ESI$^+$): 434.1 [M+H]$^+$).

Example 129

N-(6-Chloro-3-oxo-1-pyridin-2-ylmethyl-2,3-dihydro-1H-indazol-5-yl)-4-fluoro-3-trifluoromethyl-benzenesulfonamide This compound was obtained in analogy to example 32 (step B and C) using 5-nitro-1-phenyl-1,2-dihydro-indazol-3-one (prepared according to *Combinatorial Chemistry and High Throughput Screening* 2003, 6(5), 471-480) in step B and 2,4-difluorobenzenesulfonyl chloride (step C) as a light brown solid. MS (ESI$^+$): 402.3[M+H]$^+$).

Example 130

N-(6-Chloro-3-oxo-1-pyridin-2-ylmethyl-2,3-dihydro-1H-indazol-5-yl)-4-fluoro-3-trifluoromethyl-benzenesulfonamide This compound was obtained in analogy to example 32 (step B and C) using 5-nitro-1-phenyl-1,2-dihydro-indazol-3-one (prepared according to *Combinatorial Chemistry and High Throughput Screening* 2003, 6(5), 471-480) in step B and 3-chloro-2-fluorobenzenesulfonyl chloride (step C) as a light brown solid. MS (ESI$^+$): 418.2[M+H]$^+$).

Example 131

N-(1-Benzyl-6-fluoro-3-oxo-2,3-dihydro-1H-indazol-5-yl)-3-cyano-benzenesulfonamide This compound was obtained in analogy to example 32 using 2,4-difluoro-5-nitro-benzoic acid, benzylhydrazine.2HCl (step A) and 3-cyanobenzenesulfonyl chloride (step C) as a light brown solid. MS (ESI+$^-$): 423.0 [M+H]$^+$).

Example 132

Propane-2-sulfonic acid (1-benzyl-6-fluoro-3-oxo-2,3-dihydro-1H-indazol-5-yl)-amide This compound was obtained in analogy to example 32 using 2,4-difluoro-5-nitro-benzoic acid, benzylhydrazine.2HCl (step A) and 3 propane-2-sulfonyl chloride (step C) as a light brown solid. MS (ESI$^+$): 364.1 [M+H]$^+$).

Example 133

3-Cyano-N-(3-oxo-1-phenyl-2,3-dihydro-1H-indazol-5-yl)-benzenesulfonamide

This compound was obtained in analogy to example 32 (step B and C) using 5-nitro-1-phenyl-1,2-dihydro-indazol-3-one (prepared according to *Combinatorial Chemistry and High Throughput Screening* 2003, 6(5), 471-480) in step B and 3-cyanobenzenesulfonyl chloride (step C) as a light brown solid. MS (ESI$^+$): 391.1[M+H]$^+$).

Example 134

2,2,2-Trifluoro-ethanesulfonic acid (1-benzyl-6-fluoro-3-oxo-2,3-dihydro-1H-indazol-5-yl)-amide This compound was obtained in analogy to example 32 using 2,4-difluoro-5-nitro-benzoic acid, benzylhydrazine.2HCl (step A) 2,2,2-trifluoro-ethanesulfonyl chloride (step C) as a light brown solid. MS (ESI$^+$): 404.1[M+H]$^+$).

Example 135

Propane-2-sulfonic acid (1-benzyl-6-chloro-3-oxo-2,3-dihydro-1H-indazol-5-yl)-amide This compound was obtained in analogy to example 32 using 4-chloro-2-fluoro-5-nitro-benzoic acid, benzylhydrazine.2HCl (step A) and 3 propane-2-sulfonyl chloride (step C) as a light beige solid. MS (ESI$^+$): 380.1 [M+H]$^+$).

Example 136

Propane-2-sulfonic acid [6-chloro-1-(4-chloro-benzyl)-3-oxo-2,3-dihydro-1H-indazol-5-yl]-amide This compound was obtained in analogy to example 119 using 4-chlorobenzylbromide and 5-amino-6-chloro-1-(2-chloro-benzyl)-1,2-dihydro-indazol-3-one (step A) and 3 propane-2-sulfonyl chloride (step C) as a light brown solid. MS (ESI$^+$): 414.3 [M+H]$^+$).

Example 137

N-(1-Benzyl-6-fluoro-3-oxo-2,3-dihydro-1H-indazol-5-yl)-trifluoro-methanesulfonamide This compound was obtained in analogy to example 32 using 2,4-difluoro-5-nitro-benzoic acid, benzylhydrazine.2HCl (step A) and trifluoro-methanesulfonyl chloride (step C) as a light brown solid. MS (ESI$^+$): 390.1[M+H]$^+$).

Example 138

Propane-2-sulfonic acid (1-isobutyl-3-oxo-2,3-dihydro-1H-indazol-5-yl)-amide

This compound was obtained in analogy to example 32 using 5-amino-1-isobutyl-1,2-dihydro-indazol-3-one and 3 propane-2-sulfonyl chloride (step C) as a beige solid. MS (ESI$^+$): 312.1 [M+H]$^+$).

Example 139

Propane-2-sulfonic acid [1-(3,4-difluoro-benzyl)-3-oxo-2,3-dihydro-1H-indazol-5-yl]-amide This compound was obtained in analogy to example 80 using 3,4-difluorobenzylbromide (step A) and 3 propane-2-sulfonyl chloride (step C) as a light yellow solid. MS (ESI$^+$): 382.3 [M+H]$^+$).

Example 140

Propane-2-sulfonic acid [1-(2-methoxy-ethyl)-3-oxo-2,3-dihydro-1H-indazol-5-yl]-amide This compound was obtained in analogy to example 32 using (2-methoxy-ethyl)-hydrazine (step A) (prepared as described in *J. Org. Chem.* 1984, 49, 336-42) and 3 propane-2-sulfonyl chloride (step C) as a light brown solid. MS (ESI$^+$): 314.0 [M+H]$^+$).

Example 141

N-(1-Benzyl-3-oxo-2,3-dihydro-1H-indazol-5-yl)-C-cyclopropyl-methanesulfonamide

This compound was obtained in analogy to example 1 using 5-amino-1-benzyl-1,2-dihydro-indazol-3-one and cyclopropyl-methanesulfonyl chloride (step C) as a light brown solid. MS (ESI$^+$): 358.4 ([M+H]$^+$).

Example 142

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example 143

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 144

Injection solutions can have the following composition:

| Compound of formula (I) | 3.0 mg |
|---|---|
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example 145

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 146

Sachets containing the following ingredients can be manufactured in a conventional manner:

| Compound of formula (I) | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidon in water. The granulate is mixed with magnesium stearate and the flavouring additives and filled into sachets.

Example 147

Assay Procedures

Transient Expression and Partial Purification:

The cDNA encoding the human 11beta-HSD1 protein was cloned into the expression vector pcDNA3 (Stratagene). This construct (for details see Alex Odermatt et al.; J Biol Chem., 1999, Vol. 274, Issue 40, 28762-28770) was used to transiently express the protein in HEK293 cells (ATCC number: CRL-1573, described in Graham, F. L., Smiley, J., Russell, W. C., Nairn, R.; (1977)) using lipofectamine. 48 h after transfection cells were washed twice with ice-cold PBS (Phsophate buffered Saline). To 1 volume of cell suspension in PBS 2 volumes of ice-cold lysis buffer (50 mM Tris; pH7.5; 1 mM EDTA; 100 mM NaCl) were added. The cells were lysed by Potter-homogenization (20 strokes). The resulting homogenate was sonicated wit a tip sonicator (10% output; 2×30 sec.) and cleared by a low speed centrifugation (10 min×9000 g; 4° C.). The microsomal fraction was collected by a high speed centrifugation (60 min×110,000 g). The resulting pellet was resuspended in storage buffer (20 mM Tris pH 7.5; 1 mM EDTA; 10% Glycerol) and the centrifugation was repeated. The resulting pellet containing the microsomal fraction was again taken up into storage buffer and aliquots were kept frozen in liquid Nitrogen until use.

Generation of Stable Cell Lines Expressing 11beta-HSD1:

The same construct used for transient expression of human 11beta-HSD1 was also used to establish cell lines stably expressing the protein. Briefly, (HEK293) cells were transfected with 11beta-HSD1 construct using the lipofectamine reagent (Gibco BRL) according to the manufacturer's instruction. Two days after transfection, geneticin selection (0.8 mg/ml) was initiated and several stable clones were isolated. One clone was further used for pharmacological characterization.

Microsome Assay

Microsomes isolated from HEK293 cells transiently expressing human 11beta-HSD1 (for details see above) were incubated in assay buffer (100 mM NaCl; 1 mM EDTA; 1 mM EGTA; 1 mM MgCl; 250 mM Sucrose; 20 mM Tris pH 7.4; Cortisone 50-200 nM and NADPH 1 mM) together with different concentrations of test substances. After 60 min. of incubation at 37° C. the assay was stopped by heating to 80° C. (5 min.) and by addition of the inhibitor Carbenoxolone (1 uM). The amount of Cortisol produced in this assay was determined using a commercially available, ELISA-based Cortisol-detection kit (Distributed by Assay Design, Inc.). Inhibitors were characterized by there IC50 values, e.g. the concentration at which the production of cortisol was 50% reduced.

Cellular Assay

To measure the effect of inhibitors in intact cells HEK293 cells stably expressing human 11beta-HSD1 (see above) were cultivated in 96 well plates in DMEM. First inhibitors and 60 min later Cortisone was added to the cells. After 60 min of incubation at 37° C. in a 5% CO2 atmosphere part of the medium was removed and the conversion from Cortisone to Cortisol was measured using a commercially available ELISA kit (Distributed by Assay Design, Inc.).

Results obtained in the microsome assay using representative compounds of the invention as the test compounds are shown in the following table:

| Compound | h 11-beta-HSD 1 $IC_{50}$ (nM) |
| --- | --- |
| Example 2 | 0.007 |
| Example 35 | 0.101 |

Compounds as described above have $IC_{50}$ values below 1000 nM; preferred compounds have $IC_{50}$ values below 100 nM. More preferred compounds have $IC_{50}$ values below 10 nM. These results have been obtained by using the foregoing test.

It is to be understood that the invention is not limited to the particular embodiments of the invention described above, as variations of the particular embodiments may be made and still fall within the scope of the appended claims.

What is claimed is:

1. A compound of the formula (I):

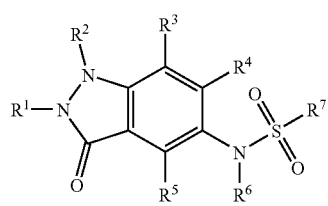

wherein:
  $R^1$ is hydrogen, lower-alkyl, aryl, or aryl-lower-alkyl;
  $R^2$ is aryl, aryl-lower-alkyl, heteroaryl, heteroaryl-lower-alkyl, cycloalkyl, cycloalkyl-lower-alkyl, fluoro-lower-alkyl, or lower-alkyl, which lower-alkyl is optionally substituted with 1 to 3 substituents selected from the group consisting of OH, CN, halogen, lower-alkoxy and $C(O)NR^8R^9$;
  $R^3$ is hydrogen, halogen, lower-alkyl, fluoro-lower-alkyl, lower-alkoxy, or fluoro-lower-alkoxy;
  $R^4$ is hydrogen, halogen, lower-alkyl, fluoro-lower-alkyl, lower-alkoxy, or fluoro-lower-alkoxy;
  $R^5$ is hydrogen, halogen, lower-alkyl, fluoro-lower-alkyl, lower-alkoxy, or fluoro-lower-alkoxy;
  $R^6$ is hydrogen or lower-alkyl;
  $R^7$ is aryl, heteroaryl, fluoro-lower-alkyl, or lower-alkyl, which lower-alkyl is optionally substituted with 1 to 3 substituents selected from the group consisting of OH, CN, halogen, lower-alkoxy and cycloalkyl; and
  $R^8$ and $R^9$, independently from each other, are selected from the group consisting of hydrogen and lower-alkyl;
and pharmaceutically acceptable salts thereof.

2. The compound according to claim 1, wherein
  $R^1$ is hydrogen, lower-alkyl, aryl, or aryl-lower-alkyl;
  $R^2$ is aryl, aryl-lower-alkyl, heteroaryl, heteroaryl-lower-alkyl, cycloalkyl, cycloalkyl-lower-alkyl, fluoro-lower-alkyl, or lower-alkyl, which lower-alkyl is optionally substituted with 1 to 3 substituents selected from the group consisting of OH, CN, halogen, lower-alkoxy and $C(O)NR^8R^9$;
  $R^3$ is hydrogen, halogen, lower-alkyl, fluoro-lower--alkyl, lower-alkoxy, or fluoro-lower-alkoxy;
  $R^4$ is hydrogen, halogen, lower-alkyl, fluoro-lower-alkyl, lower-alkoxy, or fluoro-lower-alkoxy;
  $R^5$ is hydrogen, halogen, lower-alkyl, fluoro-lower-alkyl, lower-alkoxy, or fluoro-lower-alkoxy;
  $R^6$ is hydrogen or lower-alkyl;
  $R^7$ is aryl, heteroaryl, fluoro-lower-alkyl, or lower-alkyl, which lower-alkyl is optionally substituted with 1 to 3 substituents selected from the group consisting of OH, CN, halogen and lower-alkoxy;
  $R^8$ and $R^9$, independently from each other, are selected from the group consisting of hydrogen and lower-alkyl;
and pharmaceutically acceptable salts thereof.

3. The compound according to claim 1, wherein $R^1$ is hydrogen or lower-alkyl.

4. The compound according to claim 1, wherein $R^1$ is hydrogen.

5. The compound according to claim 1, wherein $R^2$ is aryl-lower-alkyl, heteroaryl-lower-alkyl, cycloalkyl-lower-alkyl, fluoro-lower-alkyl, or lower-alkyl, which lower-alkyl is optionally substituted with 1 to 3 substituents selected from the group consisting of OH, CN, halogen, lower-alkoxy and $C(O)NR^8R^9$, wherein $R^8$ and $R^9$ are as defined in claim 1.

6. The compound according to claim 1, wherein $R^2$ is aryl-lower-alkyl or heteroaryl-lower-alkyl.

7. The compound according to claim 1, wherein $R^2$ is benzyl or pyridinylmethyl, wherein benzyl can optionally be substituted with 1 or 2 halogen.

8. The compound according to claim 1, wherein $R^2$ is benzyl, 4-fluoro-benzyl, 4-chloro-benzyl, 3,4-difluoro-benzyl, or pyridin-2-ylmethyl.

9. The compound according to claim 1, wherein $R^2$ is aryl.

10. The compound according to claim 1, wherein $R^3$ is hydrogen.

11. The compound according to claim 1, wherein $R^4$ hydrogen or halogen.

12. The compound according to claim 1, wherein $R^4$ is hydrogen, fluorine, or chlorine.

13. The compound according to claim 1, wherein $R^5$ is hydrogen or halogen.

14. The compound according to claim 1, wherein $R^5$ is hydrogen.

15. The compound according to claim 1, wherein $R^6$ is hydrogen.

16. The compound according to claim 1, wherein $R^7$ is lower-alkyl or aryl.

17. The compound according to claim 1, wherein $R^7$ is lower-alkyl, phenyl or naphthyl, wherein phenyl can optionally be substituted with 1 to 3 substituents independently selected from the group consisting of lower-alkyl, fluoro-lower-alkyl, lower-alkoxy, fluoro-lower-alkoxy, dioxo-lower-alkylene, halogen, cyano, phenoxy and 5-methyl-[1,3,4]-oxadiazol-2-yl.

18. The compound according to claim 1, wherein $R^7$ is phenyl substituted with 1 to 2 substituents selected from the group consisting of lower-alkyl, fluoro-lower-alkyl, halogen and cyano.

19. The compound according to claim 18, wherein $R^7$ is 3-chloro-2-methyl-phenyl, 2,3-dichloro-phenyl, 3-chloro-4-fluoro-phenyl, 3-trifluoromethyl-4-fluoro-phenyl, 3-cyanophenyl, 2,5-difluoro-phenyl, 3-chloro-2-fluoro-phenyl, 5-chloro-2-fluoro-phenyl, or 2-chloro-phenyl.

20. The compound according to claim 1, wherein $R^7$ is fluoro-lower-alkyl or lower-alkyl substituted with cyclopropyl.

21. The compound according to claim 20, wherein $R^7$ is cyclopropyl-methyl.

22. The compound according to claim 1, selected from the group consisting of:
- N-(1-Benzyl-3-oxo-2,3-dihydro-1H-indazol-5-yl)-3-chloro-2-methyl-benzenesulfonamide,
- N-(1-Benzyl-3-oxo-2,3-dihydro-1H-indazol-5-yl)-3-chloro-4-fluoro-benzenesulfonamide,
- N-(1-Benzyl-3-oxo-2,3-dihydro-1H-indazol-5-yl)-3 -trifluoromethyl-benzenesulfonamide,
- N-(1-Benzyl-3-oxo-2,3-dihydro-1H-indazol-5-yl)-2,4-dichloro-benzenesulfonamide,
- Naphthalene-2-sulfonic acid (1-benzyl-3-oxo-2,3-dihydro-1H-indazol-5-yl)-amide,
- N-(1-Benzyl-3-oxo-2,3-dihydro-1H-indazol-5-yl)-3-chloro-4-methyl-benzenesulfonamide,
- N-(1-Benzyl-3-oxo-2,3-dihydro-1H-indazol-5-yl)-4-methoxy-benzenesulfonamide,
- N-(1-Benzyl-3-oxo-2,3-dihydro-1H-indazol-5-yl)-2,4-dichloro-6-methyl-benzenesulfonamide,
- N-(1-Benzyl-3-oxo-2,3-dihydro-1H-indazol-5-yl)-2 -trifluoromethyl-benzenesulfonamide,
- N-(1-Benzyl-3-oxo-2,3-dihydro-1H-indazol-5-yl)-2,4-difluoro-benzenesulfonamide,
- N-(1-Benzyl-3-oxo-2,3-dihydro-1H-indazol-5-yl)-4 -propyl-benzenesulfonamide,
- 2,3-Dihydro-benzo[1,4]dioxine-6-sulfonic acid (1-benzyl-3-oxo-2,3-dihydro-1H-indazol-5-yl) -amide,
- N-(1-Benzyl-3-oxo-2,3-dihydro-1H-indazol-5-yl)-4-chloro-2,5-dimethyl-benzenesulfonamide,
- N-(1-Benzyl-3-oxo-2,3-dihydro-1H-indazol-5-yl)-4-chloro-3-trifluoromethyl-benzenesulfonamide,
- N-(1-Benzyl-3-oxo-2,3-dihydro-1H-indazol-5-yl)-4-fluoro-3-trifluoromethyl-benzenesulfonamide,
- N-(1-Benzyl-3-oxo-2,3-dihydro-1H-indazol-5-yl)-2-chloro-5-trifluoromethyl-benzenesulfonamide,
- N-(1-Benzyl-3-oxo-2,3-dihydro-1H-indazol-5-yl)-3 -phenoxy-benzenesulfonamide,
- N-(1-Benzyl-3-oxo-2,3-dihydro-1H-indazol-5-yl)-3 -(5-methyl-[1,3,4]oxadiazol-2-yl) -benzenesulfonamide,
- N-(1-Benzyl-3-oxo-2,3-dihydro-1H-indazol-5-yl)-3 -chloro-benzenesulfonamide,
- N-(1-Benzyl-3-oxo-2,3-dihydro-1H-indazol-5-yl)-3 -methoxy-benzenesulfonamide,
- N-(1-Benzyl-3-oxo-2,3-dihydro-1H-indazol-5-yl)-3 -difluoromethoxy-benzenesulfonamide,
- N-(1-Benzyl-3-oxo-2,3-dihydro-1H-indazol-5-yl)-3,5 -bis-trifluoromethyl-benzenesulfonamide,
- Propane-2-sulfonic acid (1-benzyl-3-oxo-2,3-dihydro-1H-indazol-5-yl)-amide,
- N-(1-Benzyl-3-oxo-2,3-dihydro-1H-indazol-5-yl)-3-chloro-2-N-dimethyl-benzenesulfonamide,
- N-(3-Oxo-1-propyl-2,3-dihydro-1H-indazol-5-yl)-3 -trifluoromethyl-benzenesulfonamide,
- 2,3-Dichloro-N-(3-oxo-1-propyl-2,3-dihydro-1H-indazol-5-yl) -benzenesulfonamide,
- 3-Chloro-4-fluoro-N-(3-oxo-1-propyl-2,3-dihydro-1H-indazol-5-yl)-benzenesulfonamide,
- 3-Chloro-2-methyl-#N!-(3-oxo-1-phenethyl-2,3-dihydro-1H-indazol-5-yl)-benzenesulfonamide,
- 3-Chloro-4-methyl-#N!-(3-oxo-1-phenethyl-2,3-dihydro-1H-indazol-5-yl)-benzenesulfonamide,
- 4-Chloro-2,5-dimethyl-N-(3-oxo-1-phenethyl-2,3-dihydro-1 H-indazol-5-yl)-benzenesulfonamide,
- N-(3-Oxo-1-phenethyl-2,3-dihydro-1H-indazol-5-yl)-3 -trifluoromethyl-benzenesulfonamide,
- N-(1- Isobutyl-3-oxo-2,3-dihydro-1H-indazol-5-yl)-3 -trifluoromethyl-benzenesulfonamide,
- 3-Chloro-N-(1-isobutyl-3-oxo-2,3-dihydro-1H-indazol-5-yl) -4-methyl-benzenesulfonamide,
- 3-Chloro-N-(1-isobutyl-3-oxo-2,3-dihydro-1H-indazol-5-yl) -2-methyl-benzenesulfonamide,
- 3-Cyano-(1-isobutyl-3-oxo-2,3-dihydro-indazol-5-yl) -benzenesulfonamide,
- 3-Difluoromethoxy-(1-isobutyl-3-oxo-2,3-dihydro-indazol-5-yl) -benzenesulfonamide,
- 4-Cyano-(1-isobutyl-3-oxo-2,3-dihydro-indazol-5-yl) -benzenesulfonamide,
- 4-Fluoro-N-(1-isobutyl-3-oxo-2,3-dihydro-1H-indazol-5-yl)-3-trifluoromethyl-benzenesulfonamide,
- 3-Chloro-4-fluoro-N-(1-isobutyl-3-oxo-2,3-dihydro-1H -indazol-5-yl)-benzenesulfonamide,
- 2,4-Dichloro-1-isobutyl-3-oxo-2,3-dihydro-indazol-5-yl)-5 -methyl-benzenesulfonamide,
- 3-Chloro-N-(1-ethyl-3-oxo-2,3-dihydro-1H-indazol-5-yl)-2-methyl-benzenesulfonamide,
- 3-Chloro-(1-cyclopropylmethyl-3-oxo-2,3-dihydro-indazol-5-yl)-2-methyl-benzenesulfonamide,
- 3-Chloro-(1-cyclopropylmethyl-3-oxo-2,3-dihydro-indazol-5-yl)-4-fluoro-benzenesulfonamide,
- (1-Cyclopropylmethyl-3-oxo-2,3-dihydro-indazol-5-yl)-4-fluoro-3-trifluoromethyl-benzenesulfonamide,
- 3-Chloro-(1-cyclopropylmethyl-3-oxo-2,3-dihydro-indazol-5-yl) -benzenesulfonamide,
- 2,4-Dichloro-(1-cyclopropylmethyl-3-oxo-2,3-dihydro-indazol-5-yl) -5-methyl-benzenesulfonamide,
- 3-Chloro-[1-(2-methoxy-ethyl)-3-oxo-2,3-dihydro-indazol-5 -yl]-2-methyl-benzenesulfonamide,
- 4-Fluoro-[1-(2-methoxy-ethyl)-3-oxo-2,3-dihydro-indazol-5 -yl]-3-trifluoromethyl-benzenesulfonamide,
- 3-Chloro-4-fluoro-[1-(2-methoxy-ethyl)-3-oxo-2,3-dihydro-indazol-5-yl]-benzenesulfonamide,
- 2,4-Dichloro-[1-(2-methoxy-ethyl)-3-oxo-2,3-dihydro-indazol-5-yl]-6-methyl-benzenesulfonamide,
- 3-Chloro-2-methyl-N-[3-oxo-1-(2,2,2-trifluoro-ethyl)-2,3 -dihydro-1H-indazol-5-yl]-benzenesulfonamide,
- 4-Fluoro-[3-oxo-1-(2,2,2-trifluoro-ethyl)-2,3-dihydro-indazol-5-yl]-3-trifluoromethyl-benzenesulfonamide,
- 4-Fluoro-N-(3-oxo-1-pyridin-2-ylmethyl-2,3-dihydro-1H -indazol-5-yl)-3-trifluoromethyl-benzenesulfonamide,
- 2,4-Dichloro-6-methyl-N-(3-oxo-1-pyridin-2-ylmethyl-2,3 -dihydro-1H-indazol-5-yl)-benzenesulfonamide,
- 3-Chloro-2-methyl-N-(3-oxo-1-pyridin-2-ylmethyl-2,3 -dihydro-1 H-indazol-5-yl)-benzenesulfonamide,
- 4-Fluoro-N-[1-(2-hydroxy-2-methyl-propyl)-3-oxo-2,3 -dihydro-1H-indazol-5-yl]-3 -trifluoromethyl-benzenesulfonamide,
- N-(1-Benzyl-6-chloro-3-oxo-2,3-dihydro-1H-indazol-5-yl)-3-chloro-4-fluoro-benzenesulfonamide,
- N-(1-Benzyl-6-chloro-3-oxo-2,3-dihydro-1H-indazol-5-yl)-4-fluoro-3-trifluoromethyl-benzenesulfonamide,
- N-(1-Benzyl-6-chloro-3-oxo-2,3-dihydro-1H-indazol-5-yl)-3-chloro-2-methyl-benzenesulfonamide,
- N-(1-Benzyl-6-chloro-3-oxo-2,3-dihydro-1H-indazol-5-yl)-2,3-dichloro-benzenesulfonamide,
- N-(1-Benzyl-6-chloro-3-oxo-2,3-dihydro-1H-indazol-5-yl)-3-cyano-benzenesulfonamide,
- N-(1-Benzyl-6-chloro-3-oxo-2,3-dihydro-1H-indazol-5-yl)-3-chloro-benzenesulfonamide, N-(1-Benzyl-6-chloro-3-oxo-2,3-dihydro-1H-indazol-5-yl)-4-chloro-3-trifluoromethyl-benzenesulfonamide,
N-(1-Benzyl-6-chloro-3-oxo-2,3-dihydro-1H-indazol-5-yl)-3-difluoromethoxy-benzenesulfonamide,
N-(1-Benzyl-6-chloro-3-oxo-2,3-dihydro-1H-indazol-5-yl)-2-trifluoromethyl-benzenesulfonamide,
N-(1-Benzyl-6-chloro-3-oxo-2,3-dihydro-1H-indazol-5-yl)-3-trifluoromethoxy-benzenesulfonamide,
N-(1-Benzyl-6-chloro-3-oxo-2,3-dihydro-1H-indazol-5-yl)-2,5-difluoro-benzenesulfonamide,
N-(1-Benzyl-6-chloro-3-oxo-2,3-dihydro-1H-indazol-5-yl)-2,4-dichloro-benzenesulfonamide,
N-(1-Benzyl-6-chloro-3-oxo-2,3-dihydro-1H-indazol-5-yl)-3-chloro-2-fluoro-benzenesulfonamide,
N-(1-Benzyl-6-chloro-3-oxo-2,3-dihydro-1H-indazol-5-yl)-3-trifluoromethyl-benzenesulfonamide,
N-(1-Benzyl-6-chloro-3-oxo-2,3-dihydro-1H-indazol-5-yl)-5-chloro-2-fluoro-benzenesulfonamide,
N-(1-Benzyl-6-chloro-3-oxo-2,3-dihydro-1H-indazol-5-yl)-2-chloro-benzenesulfonamide, (1-Benzyl-4-chloro-3-oxo-2,3-dihydro-indazol-5-yl)-3-chloro-2-methyl-benzenesulfonamide,
N-(1-Benzyl-6-fluoro-3-oxo-2,3-dihydro-1H-indazol-5-yl)-4-fluoro-3-trifluoromethyl-benzenesulfonamide,
N-(1-Benzyl-6-fluoro-3-oxo-2,3-dihydro-1H-indazol-5-yl)-2,3-dichloro-benzenesulfonamide,
N-(1-Benzyl-6-fluoro-3-oxo-2,3-dihydro-1H-indazol-5-yl)-2,4-dichloro-benzenesulfonamide,
N-(1-Benzyl-6-fluoro-3-oxo-2,3-dihydro-1H-indazol-5-yl)-3-chloro-2-fluoro-benzenesulfonamide,
N-( 1-Benzyl-6-fluoro-3-oxo-2,3-dihydro-1H-indazol-5-yl)-5-chloro-2-fluoro-benzenesulfonamide,
N-(1-Benzyl-6-fluoro-3-oxo-2,3-dihydro-1H-indazol-5-yl)-3-trifluoromethoxy-benzenesulfonamide,
3-Chloro-N-[1-(4-fluoro-benzyl)-3-oxo-2,3-dihydro-1H-indazol-5-yl]-benzenesulfonamide,
3-Difluoromethoxy-N-[1-(4-fluoro-benzyl)-3-oxo-2,3-dihydro-1H-indazol-5-yl]-benzenesulfonamide,
4-Fluoro-N-[1-(4-fluoro-benzyl)-3-oxo-2,3-dihydro-1H-indazol-5-yl]-3-trifluoromethyl-benzenesulfonamide,
2,3-Dihydro-benzo[1,4]dioxine-6-sulfonic acid [1-(4-fluoro-benzyl)-3-oxo-2,3-dihydro-1H-indazol-5-yl]-amide,
2,4-Dichloro-N-[1-(4-fluoro-benzyl)-3-oxo-2,3-dihydro-1H-indazol-5-yl]-6-methyl-benzenesulfonamide,
5-Chloro-2,4-difluoro-N-[1-(4-fluoro-benzyl)-3-oxo-2,3-dihydro-1H-indazol-5-yl]-benzenesulfonamide,
4-Chloro-2,5-difluoro-N-[1-(4-fluoro-benzyl)-3-oxo-2,3-dihydro-1H-indazol-5-yl]-benzenesulfonamide,
3-Chloro-[1-(4-fluoro-benzyl)-3-oxo-2,3-dihydro-indazol-5-yl]-2-methyl-benzenesulfonamide,
3-Cyano-[1-(4-fluoro-benzyl)-3-oxo-2,3-dihydro-indazol-5-yl]-benzenesulfonamide,
Naphthalene-1-sulfonic acid [1-(4-fluoro-benzyl)-3-oxo-2,3-dihydro-1H-indazol-5-yl]-amide,
3-Chloro-4-fluoro-N-[1-(4-fluoro-benzyl)-3-oxo-2,3-dihydro-1H-indazol-5-yl]-benzenesulfonamide,
3-Chloro-[1-(3,4-difluoro-benzyl)-3-oxo-2,3-dihydro-indazol-5-yl]-2-methyl-benzenesulfonamide,
3-Chloro-[1-(3,4-difluoro-benzyl)-3-oxo-2,3-dihydro-indazol-5-yl]-4-fluoro-benzenesulfonamide,
[1-(3,4-Difluoro-benzyl)-3-oxo-2,3-dihydro-indazol-5-yl]-4-fluoro-3-trifluoromethyl-benzenesulfonamide,
3-Chloro-[1-(3,4-difluoro-benzyl)-3-oxo-2,3-dihydro-indazol-5-yl]-benzenesulfonamide,
[1-(3,4-Difluoro-benzyl1)-3-oxo-2,3-dihydro-indazol-5-yl]-3-trifluoromethoxy-benzenesulfonamide,
2,4-Dichloro-[1-(3,4-difluoro-benzyl)-3-oxo-2,3-dihydro-indazol-5-yl]-5-methyl-benzenesulfonamide,
3,4-Dichloro-[1-(3,4-difluoro-benzyl)-3-oxo-2,3-dihydro-indazol-5-yl]-benzenesulfonamide,
4,5-Dichloro-[1-(3,4-difluoro-benzyl)-3-oxo-2,3-dihydro-indazol-5-yl]-2-fluoro-benzenesulfonamide,
2,4,5-Trichloro-[1-(3,4-difluoro-benzyl)-3-oxo-2,3-dihydro-indazol-5-yl]-benzenesulfonamide,
2,3-Dichloro-[1-(3,4-difluoro-benzyl)-3-oxo-2,3-dihydro-indazol-5-yl]-benzenesulfonamide,
2,4-Dichloro-[1-(3,4-difluoro-benzyl)-3-oxo-2,3-dihydro-indazol-5-yl]-6-methyl-benzenesulfonamide,
3-Chloro-N-[1-(2,4-difluoro-benzyl)-3-oxo-2,3-dihydro-1H-indazol-5-yl]-4-fluoro-benzenesulfonamide,
N-[1-(2,4-Difluoro-benzyl)-3-oxo-2,3-dihydro-1H-indazol-5-yl]-4-fluoro-3-trifluoromethyl-benzenesulfonamide,
3-Chloro-N-[1-(2,4-difluoro-benzyl)-3-oxo-2,3-dihydro-1H-indazol-5-yl]-2-methyl-benzenesulfonamide,
N-[1-(4-Chloro-benzyl)-3-oxo-2,3-dihydro-1H-indazol-5-yl]-4-fluoro-3-trifluoromethyl-benzenesulfonamide,
3-Chloro-N-[1-(4-chloro-benzyl)-3-oxo-2,3-dihydro-1H-indazol-5-yl]-2-methyl-benzenesulfonamide,
2,3-Dichloro-N-[1-(4-chloro-benzyl)-3-oxo-2,3-dihydro-1H-indazol-5-yl]-benzenesulfonamide,
Naphthalene-1-sulfonic acid [1-(4-chloro-benzyl)-3-oxo-2,3-dihydro-1H-indazol-5-yl]-amide,
3-Chloro-N-[1-(2-chloro-4-fluoro-benzyl)-3-oxo-2,3-dihydro-1H-indazol-5-yl]-2-methyl-benzenesulfonamide,
Naphthalene-1-sulfonic acid [1-(2-chloro-4-fluoro-benzyl)-3-oxo-2,3-dihydro-1H-indazol-5-yl]-amide,
2,3-Dichloro-N-[1-(2-chloro-4-fluoro-benzyl)-3-oxo-2,3-dihydro-1H-indazol-5-yl]-benzenesulfonamide,
N-[1-(2-Chloro-4-fluoro-benzyl)-3-oxo-2,3-dihydro-1H-indazol-5-yl]-4-fluoro-3-trifluoromethyl-benzenesulfonamide,
N-[1-(2-Chloro-4-fluoro-benzyl)-3-oxo-2,3-dihydro-1H-indazol-5-yl]-3-difluoromethoxy-benzenesulfonamide,
N-[1-(2-Chloro-4-fluoro-benzyl)-3-oxo-2,3-dihydro-1H-indazol-5-yl]-3-trifluoromethoxy-benzenesulfonamide,
3-Chloro-N-[1-(2-cyano-ethyl)-3-oxo-2,3-dihydro-1H-indazol-5-yl]-2-methyl-benzenesulfonamide,
N-[1-(2-Cyano-ethyl)-3-oxo-2,3-dihydro-1H-indazol-5-yl]-4-fluoro-3-trifluoromethyl-benzenesulfonamide,
2,4-Dichloro-N-[1-(2-cyano-ethyl)-3-oxo-2,3-dihydro-1H-indazol-5-yl]-6-methyl-benzenesulfonamide,
3-Chloro-N-[1-(2-cyano-ethyl)-3-oxo-2,3-dihydro-1H-indazol-5-yl]-4-fluoro-benzenesulfonamide,
N-[6-Chloro-1-(2-chloro-benzyl)-3-oxo-2,3-dihydro-1H-indazol-5-yl]-4-fluoro-3-trifluoromethyl-benzenesulfonamide,
5-Chloro-N-[6-chloro-1-(2-chloro-benzyl)-3-oxo-2,3-dihydro-1H-indazol-5-yl]-2-fluoro-benzenesulfonamide,
2,3-Dichloro-N-[6-chloro-1-(2-chloro-benzyl)-3-oxo-2,3-dihydro-1H-indazol-5-yl]-benzenesulfonamide,
3-Chloro-N-(6-chloro-3-oxo-1-pyridin-2-ylmethyl-2,3-dihydro-1H-indazol-5-yl)-2-methyl-benzenesulfonamide,
N-(6-Chloro-3-oxo-1-pyridin-2-ylmethyl-2,3-dihydro-1H-indazol-5-yl)-4-fluoro-3-trifluoromethyl-benzenesulfonamide,
2-[5-(3-Chloro-2-methyl-benzenesulfonylamino)-3-oxo-2,3-dihydro-indazol-5-yl]-methyl-acetamide, 2,4-Dichloro-[1-(3,4-difluoro-benzyl)-2-methyl-3-oxo-2,3-dihydro-indazol-5-yl]-6-methyl-benzenesulfonamide, and
3-Chloro-[1-(3,4-difluoro-benzyl)-2-methyl-3-oxo-2,3-dihydro-indazol-5-yl]-2-methyl-benzenesulfonamide,
and pharmaceutically acceptable salts thereof.

23. The compound according to claim 1, selected from the group consisting of:
N-(1-Benzyl-6-chloro-3-oxo-2,3-dihydro-1H-indazol-5-yl)-3-chloro-2-methyl-benzenesulfonamide,
N-(1-Benzyl-6-chloro-3-oxo-2,3-dihydro-1H-indazol-5-yl)-2,5-difluoro-benzenesulfonamide,
N-(1-Benzyl-6-chloro-3-oxo-2,3-dihydro-1H-indazol-5-yl)-3-chloro-2-fluoro-benzenesulfonamide,
N-(1-Benzyl-6-chloro-3-oxo-2,3-dihydro-1H-indazol-5-yl)-2-chloro-benzenesulfonamide,
N-(1-Benzyl-6-fluoro-3-oxo-2,3-dihydro-1H-indazol-5-yl)-3-chloro-2-fluoro-benzenesulfonamide,
N-(1-Benzyl-6-fluoro-3-oxo-2,3-dihydro-1H-indazol-5-yl)-2,3-dichloro-benzenesulfonamide,
N-(1-Benzyl-6-fluoro-3-oxo-2,3-dihydro-1H-indazol-5-yl)-5-chloro-2-fluoro-benzenesulfonamide,
N-(1-Benzyl-3-oxo-2,3-dihydro-1H-indazol-5-yl)-3-chloro-2-methyl-benzenesulfonamide,
3-Cyano-[1-(4-fluoro-benzyl)-3-oxo-2,3-dihydro-indazol-5-yl]-benzenesulfonamide,
2,3-Dichloro-N-[1-(4-chloro-benzyl)-3-oxo-2,3-dihydro-1H-indazol-5-yl]-benzenesulfonamide,
3-Chloro-N-[1-(4-chloro-benzyl)-3-oxo-2,3-dihydro-1H-indazol-5-yl]-2-methyl-benzenesulfonamide,
4-Fluoro-N-[1-(4-fluoro-benzyl)-3-oxo-2,3-dihydro-1H-indazol-5-yl]-3-trifluoromethyl-benzenesulfonamide,
3-Chloro-4-fluoro-N-[1-(4-fluoro-benzyl)-3-oxo-2,3-dihydro-1H-indazol-5-yl]-benzenesulfonamide,
3-Chloro-[1-(3,4-difluoro-benzyl)-3-oxo-2,3-dihydro-indazol-5-yl]-2-methyl-benzenesulfonamide,
N-[1-(4-Chloro-benzyl)-3-oxo-2,3-dihydro-1H-indazol-5-yl]-4-fluoro-3-trifluoromethyl-benzenesulfonamide, and
3-Chloro-2-methyl-N-(3-oxo-1-pyridin-2-ylmethyl-2,3-dihydro-1#H!-indazol-5-yl)-benzenesulfonamide,
and pharmaceutically acceptable salts thereof.

24. The compound according to claim 1, selected from the group consisting of:
2,3-Dichloro-N-(6-chloro-3-oxo-1-pyridin-2-ylmethyl-2,3-dihydro-1H-indazol-5-yl)-benzenesulfonamide,
N-(1-Benzyl-6-fluoro-3-oxo-2,3-dihydro-1H-indazol-5-yl)-2,4-difluoro-benzenesulfonamide,
2,4-Difluoro-N-(3-oxo-1-phenyl-2,3-dihydro-1H-indazol-5-yl)-benzenesulfonamide,
3-Chloro-2-fluoro-N-(3-oxo-1-phenyl-2,3-dihydro-1H-indazol-5-yl)-benzenesulfonamide,
N-(1-Benzyl-6-fluoro-3-oxo-2,3-dihydro-1H-indazol-5-yl)-3-cyano-benzenesulfonamide,
Propane-2-sulfonic acid (1-benzyl-6-fluoro-3-oxo-2,3-dihydro-1H-indazol-5-yl)-amide,
3-Cyano-N-(3-oxo-1-phenyl-2,3-dihydro-1H-indazol-5-yl)-benzenesulfonamide,
2,2,2-Trifluoro-ethanesulfonic acid (1-benzyl-6-fluoro-3-oxo-2,3-dihydro-1H-indazol-5-yl)-amide,
Propane-2-sulfonic acid (1-benzyl-6-chloro-3-oxo-2,3-dihydro-1H-indazol-5-yl)-amide,
Propane-2-sulfonic acid [6-chloro-1-(4-chloro-benzyl)-3-oxo-2,3-dihydro-1H-indazol-5-yl]-amide,
N-(1-Benzyl-6-fluoro-3-oxo-2,3-dihydro-1H-indazol-5-yl)-trifluoro-methanesulfonamide,
Propane-2-sulfonic acid (1-isobutyl-3-oxo-2,3-dihydro-1H-indazol-5-yl)-amide,
Propane-2-sulfonic acid [1-(3,4-difluoro-benzyl)-3-oxo-2,3-dihydro-1H-indazol-5-yl]-amide,
Propane-2-sulfonic acid [1-(2-methoxy-ethyl)-3-oxo-2,3-dihydro-1H-indazol-5-yl]-amide, and
N-(1-Benzyl-3-oxo-2,3-dihydro-1H-indazol-5-yl)-C-cyclopropyl-methanesulfonamide
and pharmaceutically acceptable salts thereof.

25. The compound according to claim 1, which is:
N-(1-Benzyl-3-oxo-2,3-dihydro-1H-indazol-5-yl)-C-cyclopropyl-methanesulfonamide
and pharmaceutically acceptable salts thereof.

26. A process for the preparation of compounds according to claim 1, comprising the reaction of a compound of formula (II)

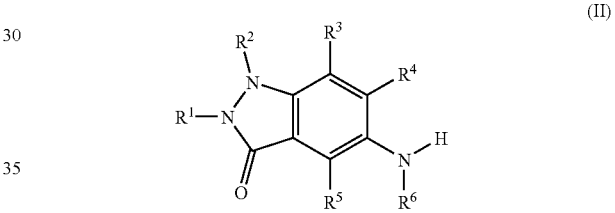

with a compound of formula (III)

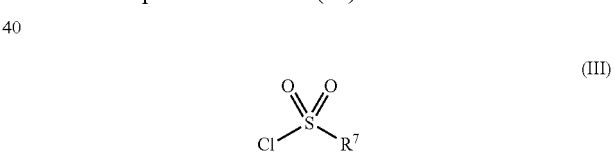

wherein $R^1$ to $R^7$ are as defined in claim 1.

27. A pharmaceutical composition, comprising a therapeutically effective amount of a compound according to claim 1 and a pharmaceutically acceptable carrier and/or adjuvant.

28. A method for the treatment of type II diabetes mellitus and metabolic syndrome, comprising the step of administering an effective amount of a compound as defined in claim 1 to a patient in need thereof.

* * * * *